(12) United States Patent
Akhtari

(10) Patent No.: US 10,197,657 B2
(45) Date of Patent: Feb. 5, 2019

(54) METHODS AND SYSTEMS FOR GENERATING A CONDUCTIVITY MAP OF AN IN VIVO TISSUE

(71) Applicant: The Regents of the University of California, Oakland, CA (US)

(72) Inventor: Massoud Akhtari, Pasadena, CA (US)

(73) Assignee: The Regents of the University of California, Oakland, CA (US)

(*) Notice: Subject to any disclaimer, the term of this patent is extended or adjusted under 35 U.S.C. 154(b) by 371 days.

(21) Appl. No.: 15/233,448

(22) Filed: Aug. 10, 2016

(65) Prior Publication Data

US 2017/0045601 A1 Feb. 16, 2017

Related U.S. Application Data

(60) Provisional application No. 62/204,271, filed on Aug. 12, 2015.

(51) Int. Cl.
*A61B 5/05* (2006.01)
*G01R 33/563* (2006.01)
*A61B 5/055* (2006.01)
*A61B 5/00* (2006.01)

(52) U.S. Cl.
CPC ...... *G01R 33/56341* (2013.01); *A61B 5/0042* (2013.01); *A61B 5/0044* (2013.01); *A61B 5/055* (2013.01); *A61B 5/7278* (2013.01)

(58) Field of Classification Search
CPC ............ G01R 33/56341; A61B 5/7278; A61B 5/0042; A61B 5/055; A61B 5/0044
See application file for complete search history.

(56) References Cited

U.S. PATENT DOCUMENTS

| | | | |
|---|---|---|---|
| 2014/0184219 A1* | 7/2014 | Kim | G01R 33/48 324/309 |
| 2014/0300354 A1* | 10/2014 | He | G01R 33/443 324/309 |
| 2015/0051475 A1* | 2/2015 | Leussler | G01R 33/4804 600/411 |
| 2016/0055304 A1* | 2/2016 | Russell | G06F 19/3412 705/3 |
| 2016/0305910 A1* | 10/2016 | Driscoll | G01V 3/08 |
| 2017/0303991 A1* | 10/2017 | Rubinsky | G01R 33/4804 |
| 2018/0011158 A1* | 1/2018 | Katscher | A61B 5/055 |

OTHER PUBLICATIONS

Emin, et al., Ionic charge transport between blockages: Sodium cation conduction in freshly excised bulk brain tissue, AIP Advances 5, 087133 (2015), 7 pages.

* cited by examiner

*Primary Examiner* — Sanjay Cattungal
(74) *Attorney, Agent, or Firm* — Bozicevic Field & Francis, LLP; Paula A. Borden

(57) ABSTRACT

The present disclosure provides methods of generating a conductivity map of an in vivo tissue. The present disclosure provides systems for generating a conductivity map of an in vivo tissue.

18 Claims, 14 Drawing Sheets

FIG. 2

| patient | Field Strength (T) | TR (ms) | TE (ms) | Slice Thickness (mm) | FOV (mm) | matrix | Directions | b-value |
|---|---|---|---|---|---|---|---|---|
| 1 | 1.5 | 1.00E+04 | 78 | 2 | 240x240 | 128x128 | 6 | 700 |
| 2 | 1.5 | 1.00E+04 | 78 | 2 | 240x240 | 128x128 | 6 | 700 |
| 3 | 1.5 | 1.00E+04 | 78 | 2 | 240x240 | 128x128 | 6 | 700 |
| 4 | 1.5 | 1.00E+04 | 78 | 2 | 240x240 | 128x128 | 6 | 700 |
| 5 | 1.5 | 1.00E+04 | 78 | 2 | 240x240 | 128x128 | 6 | 700 |
| 6 | 1.5 | 7.70E+03 | 129 | 4 | 200x200 | 128x128 | 12 | 1200, 600 |
| 7 | 1.5 | 1.00E+04 | 97.8 | 4 | 220x220 | 128x128 | 12 | 1000 |
| 8 | 1.5 | 1.00E+04 | 78 | 2 | 256x256 | 128x128 | 6 | 700 |
| 9 | 1.5 | 1.00E+04 | 88.5 | 4 | 260x260 | 128x128 | 12 | 1000 |
| 10 | 3 | 4.70E+03 | 96 | 4 | 180x180 | 128x128 | 12 | 1200, 600 |
| 11 | 3 | 4.50E+03 | 93 | 4 | 200x200 | 128x128 | 12 | 1200, 600 |
| 12 | 1.5 | 1.00E+04 | 107 | 4 | 260x260 | 128x128 | 12 | 1000 |
| 13 | 3 | 9.10E+03 | 87 | 2 | 256x256 | 128x128 | 12 | 1200, 600 |
| 14 | 1.5 | 1.00E+04 | 102.1 | 4 | 250x250 | 128x128 | 12 | 1000 |
| 15 | 3 | 4.71E+03 | 93 | 4 | 200x200 | 128x128 | 12 | 1200, 600 |
| 16 | 1.5 | 5.40E+03 | 90 | 4 | 200x200 | 128x128 | 12 | 1200, 600 |
| 17 | 3 | 4.70E+03 | 96 | 4 | 180x180 | 128x128 | 12 | 1200, 600 |
| 18 | 3 | 4.80E+03 | 93 | 4 | 200x200 | 128x128 | 12 | 1200, 600 |
| 19 | 1.5 | 5.40E+03 | 90 | 4 | 200x200 | 128x128 | 12 | 1200, 600 |
| 20 | 3 | 4.50E+03 | 93 | 4 | 200x200 | 128x128 | 12 | 1200, 600 |
| 21 | 1.5 | 8.00E+03 | 129 | 4 | 180x180 | 128x128 | 12 | 1200, 600 |
| 22 | 3 | 4.50E+03 | 93 | 4 | 200x200 | 128x128 | 12 | 1200, 600 |
| 23 | 3 | 5.40E+03 | 93 | 4 | 200x200 | 128x128 | 12 | 1200, 600 |
| 24 | 3 | 4.50E+03 | 93 | 4 | 200x200 | 128x128 | 12 | 1200, 600 |

FIG. 4

| Variable | $\sigma_\perp$ | $\sigma_\parallel$ | $\sigma_\parallel/\sigma_\perp$ | $D_\perp$ | $D_\parallel$ | $D_\parallel/D_\perp$ |
|---|---|---|---|---|---|---|
| Age Seizure Onset | 0.40/0.534 | 1.70/0.202 | 0.56/0.462 | 4.20/0.053 | 5.40/0.030 | 0.08/0.774 |
| Age at Surgery | 0.04/0.834 | 0.62/0.440 | 0.55/0.468 | 6.58/0.018 | 7.71/0.011 | 0.38/0.544 |
| Epilepsy Duration | 0.12/0.732 | 0.01/0.913 | 0.17/0.687 | 3.38/0.080 | 3.40/0.079 | 0.52/0.479 |
| Gender | 0.01/0.974 | 1.60/0.215 | 2.80/0.108 | 0.43/0.518 | 2.86/0.105 | 2.18/0.154 |
| Side Removed | 0.15/0.698 | 0.13/0.720 | 0.16/0.690 | 1.16/0.292 | 2.50/0.128 | 0.12/0.736 |
| H/O Infantile Spasms | 0.01/0.948 | 0.22/0.642 | 0.34/0.565 | 2.62/0.119 | 2.53/0.126 | 0.56/0.460 |
| CD vs. Non-CD Etiology | 0.61/0.442 | 0.74/0.398 | 0.06/0.810 | 0.01/0.951 | 0.38/0.543 | 0.77/0.389 |
| Daily vs. Less than Daily Sz Frequency | 0.41/0.526 | 2.30/0.143 | 0.85/0.366 | 0.32/0.576 | 1.19/0.288 | 0.29/0.597 |
| Sz Free Post-surgery | 0.01/0.976 | 0.20/0.660 | 1.02/0.509 | 0.06/0.806 | 0.84/0.371 | 5.36/0.031 |

FIG. 5

| patient | $\sigma_\perp$ (mS/m) | %δσsys | $\sigma_\parallel$ | %δσsys | $D_\perp$ ($10^{-5}$ cm$^2$/s) | SD | $D_{max}$ | SD | $D_{max}/D_\perp$ | ADC ×10$^{-3}$ |
|---|---|---|---|---|---|---|---|---|---|---|
| 1 | 62.6 | 9.8 | 66.9 | 9 | 1.08 | 0.46 | 1.178 | 0.5 | 1.348 | 1.063 |
| 2 | 137.5 | 4.7 | 119 | 5.3 | 1.033 | 0.36 | 1.156 | 0.3 | 1.260 | 1.045 |
| 3 | 97.6 | 6.3 | 99.8 | 6.2 | 1.224 | 0.26 | 1.375 | 0.3 | 1.389 | 1.22 |
| 4 | 80.5 | 7.6 | 98.2 | 6.4 | 1.17 | 0.44 | 1.285 | 0.5 | 1.212 | 1.192 |
| 5 | 109.2 | 5.7 | 90.8 | 6.8 | 1.28 | 0.34 | 1.123 | 0.3 | 1.208 | 1.125 |
| 6 | 116.8 | 5.4 | 110.2 | 5.6 | 1.041 | 0.24 | 1.235 | 0.2 | 1.238 | 1.104 |
| 7 | 243.2 | 3.2 | 185.3 | 3.6 | 1.242 | 0.38 | 1.331 | 0.4 | 1.227 | 1.227 |
| 8 | 104.7 | 6 | 107.9 | 5.7 | 1.206 | 0.57 | 1.246 | 0.4 | 1.451 | 1.142 |
| 9 | 96 | 6.4 | 103.2 | 5.9 | 0.948 | 0.35 | 1.152 | 0.4 | 1.291 | 1.063 |
| 10 | 97.8 | 6.4 | 103.1 | 6.1 | 1.136 | 0.24 | 1.37 | 0.3 | 1.398 | 1.205 |
| 11 | 86 | 7.1 | 106.1 | 6.2 | 1.061 | 0.24 | 1.119 | 0.3 | 1.275 | 1.036 |
| 12 | 136.6 | 4.8 | 111 | 5.7 | 0.968 | 0.29 | 1.106 | 0.3 | 1.258 | 1.001 |
| 13 | 124.1 | 5.2 | 132 | 4.6 | 0.792 | 0.3 | 0.655 | 0.3 | 1.243 | 1.061 |
| 14 | 163.4 | 4.2 | 118.9 | 5.3 | 1.229 | 0.53 | 1.246 | 0.5 | 1.197 | 1.187 |
| 15 | 191.9 | 3.6 | 137.6 | 4.6 | 0.72 | 0.22 | 0.634 | 0.4 | 1.342 | 9.732 |
| 16 | 69.6 | 8.8 | 76.3 | 7.9 | 1.103 | 0.28 | 1.15 | 0.3 | 1.191 | 1.081 |
| 17 | 116.5 | 5.4 | 120.8 | 5.3 | 1.124 | 0.3 | 1.172 | 0.3 | 1.290 | 1.094 |
| 18 | 100.1 | 6.1 | 119.8 | 5.3 | 1.108 | 0.3 | 1.13 | 0.3 | 1.218 | 1.079 |
| 19 | 161.3 | 3.8 | 164.6 | 4.1 | 1.093 | 0.14 | 1.169 | 0.2 | 1.260 | 1.064 |
| 20 | 97.8 | 6.3 | 129.2 | 5 | 1.12 | 0.57 | 1.289 | 0.5 | 1.253 | 1.179 |
| 21 | 103.9 | 6 | 98.7 | 6.2 | 1.147 | 0.39 | 1.298 | 0.4 | 1.293 | 1.177 |
| 22 | 128.1 | 5 | 112.2 | 5.6 | 0.997 | 0.59 | 1.139 | 0.7 | 1.411 | 1.02 |
| 23 | 101.1 | 6.2 | 152.4 | 4.4 | 1.411 | 0.71 | 1.463 | 0.7 | 1.165 | 1.048 |
| 24 | 85.3 | 7.2 | 54.3 | 11 | 0.708 | 0.31 | 0.846 | 0.3 | 1.385 | 0.0992 |

FIG. 6

| Variable | $\sigma_\parallel$ | $D\perp$ | $D_\parallel$ | $D_\parallel/D\perp$ |
|---|---|---|---|---|
| $\sigma\perp$ | +0.79/<0.0001 | 0.09/0.676 | 0.08/0.706 | 0.06/0.738 |
| $\sigma_\parallel$ | | 0.18/0.378 | 0.23/0.278 | 0.02/0.913 |
| $\sigma_\parallel/\sigma\perp$ | | +0.45/0.027 | +0.48/0.017 | 0.10/0.639 |
| $D\perp$ | | | +0.88/<0.0001 | |

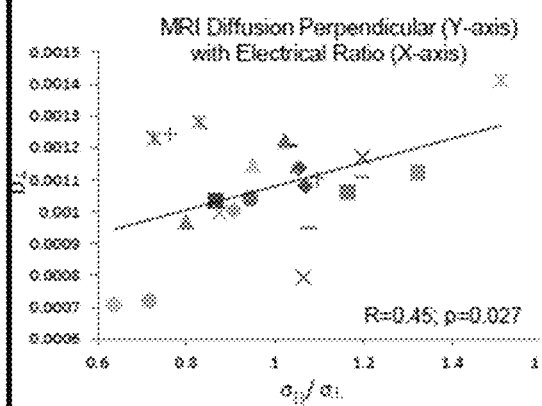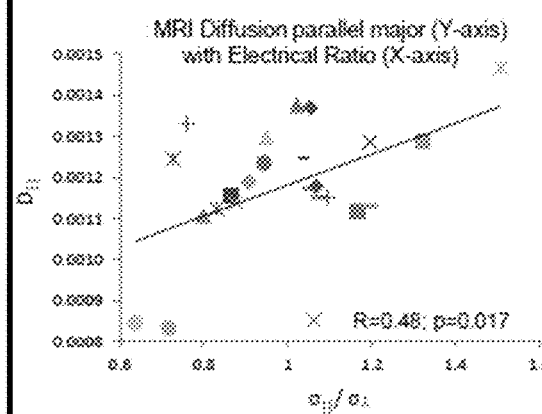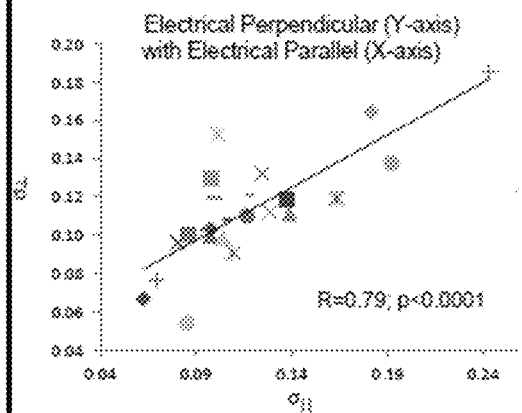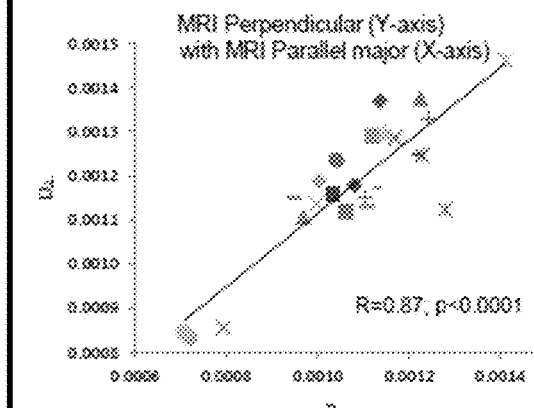

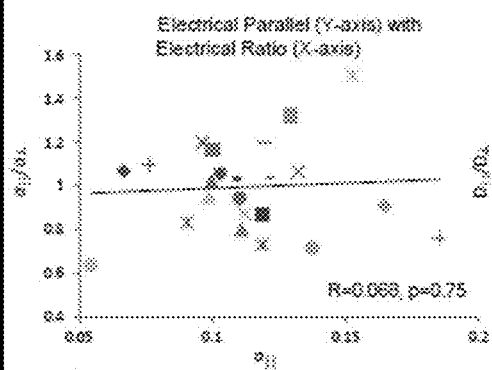
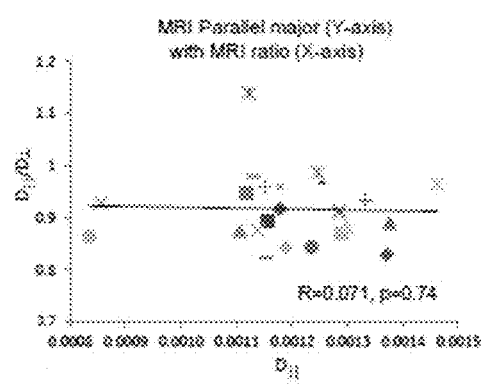
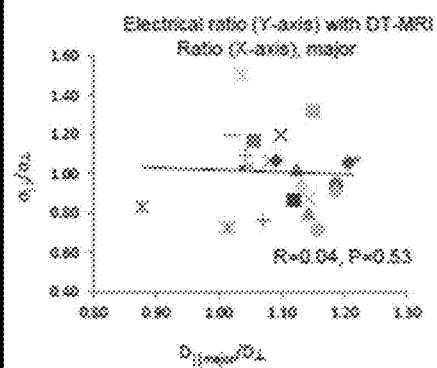
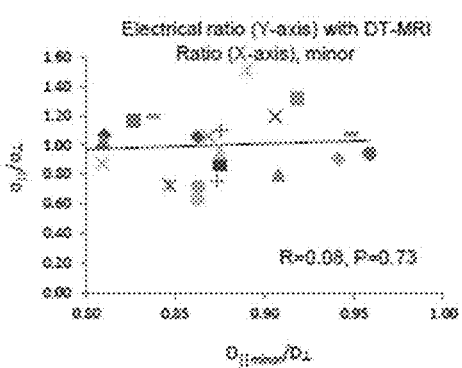

METHODS AND SYSTEMS FOR GENERATING A CONDUCTIVITY MAP OF AN IN VIVO TISSUE

CROSS-REFERENCE TO RELATED APPLICATIONS

This application claims priority under 35 U.S.C. § 119 to U.S. Provisional Application No. 62/204,271, filed Aug. 12, 2015, the disclosure of which is incorporated herein by reference.

STATEMENT REGARDING FEDERALLY SPONSORED RESEARCH

This invention was made with government support under Grant No. NS060675-01 awarded by The National Institutes of Health. The government has certain rights in the invention.

INTRODUCTION

Quantitative intracranial current source localization using mathematical models applied to magnetoencephalography (MEG), electroencephalography (EEG), and combined MEG-EEG data rely on assumptions regarding electrical conductivity through the skull and brain. In particular, quantitative estimates of electrical conductivities and tissue anisotropies are needed for accurate boundary element, finite element, single and multi-sphere models, and combination MEG/EEG models, as mis specification of these conductivity parameters and their anisotropies can affect the apparent magnitude (strength) of magnetic fields and electric surface potentials, leading to inappropriate localization.

Recently, diffusion tensor magnetic resonance imaging (DT-MRI) has been studied as a potential surrogate imaging biomarker for electrical conductivity in cerebral tissues. DT-MRI is a magnetic resonance imaging (MRI) technique that provides quantitative and directionally sensitive measurements of the apparent diffusion coefficient (ADC) of water protons.

There is a need in the art for methods of generating conductivity maps of in vivo tissues.

SUMMARY

The present disclosure provides methods of generating a conductivity map of an in vivo tissue. The present disclosure provides systems for generating a conductivity map of an in vivo tissue.

Aspects of the present disclosure include a non-invasive method of generating a conductivity map of an in vivo tissue. The method includes: a) measuring a concentration of a carrier ion in the tissue using magnetic resonance imaging (MRI); b) measuring a water proton diffusivity (D) in the tissue using diffusion tensor MRI (DT-MRI); and c) generating a conductivity map of the tissue, using the formula: $\sigma = (D\ n\ q^2)/kT$, wherein $\sigma$ is conductivity, D is the water proton diffusivity, n is the concentration of the carrier ion, q is a charge of the carrier ion, k is Boltzmann constant, and T is temperature in degrees Kelvin.

In some embodiments, the tissue is brain tissue.

In some embodiments, the tissue is heart tissue.

In some embodiments, concentration of the carrier ion and the water proton diffusivity are measured using a single coil.

In some embodiments, the carrier ion is selected from sodium ion, chloride ion, potassium ion, and calcium ion.

In some embodiments, the DT-MRI is performed at 0.3 T.
In some embodiments, the DT-MRI is performed at 1.5 T.
In some embodiments, the DT-MRI is performed at 3 T.
In some embodiments, the DT-MRI is performed at 7 T.
In some embodiments, the DT-MRI is performed at 9 T.
In some embodiments, the DT-MRI is performed at 12 T.

Aspects of the present disclosure include a system for generating a conductivity map of an in vivo tissue. The system includes: a) a magnetic resonance imaging (MRI) device configured to measure a concentration of a carrier ion in the tissue and a water proton diffusivity (D) in the tissue; b) a processor; and c) a non-transient memory comprising instructions that, when executed by the processor, cause the processor to generate a conductivity map of the tissue based on measurements from the MRI device, wherein the instructions comprise the formula: $\sigma = (D\ n\ q^2)/kT$, wherein $\sigma$ is conductivity, D is the water proton diffusivity, n is the concentration of the carrier ion, q is the charge of the carrier ion, k is Boltzmann constant, and T is temperature in degrees Kelvin.

In some embodiments, the system includes a data storage that is configured to store conductivity map data.

In some embodiments, the system includes a user interface and a data connector that transmits data between the processor and the user interface.

In some embodiments, the MRI device comprises a coil for measuring the concentration of the carrier ion in the tissue.

In some embodiments, the MRI device comprises electronic devices configured to generate frequencies, gradients and pulses for measuring the concentration of the carrier ion in the tissue.

In some embodiments, the MRI device comprises a coil for measuring the water proton diffusivity (D) in the tissue.

In some embodiments, the MRI device comprises a single coil for measuring the concentration of the carrier ion in the tissue and the water proton diffusivity (D) in the tissue.

BRIEF DESCRIPTION OF THE DRAWINGS

FIG. 2 depicts a table showing the DT-MRI field strength and acquisition parameters for the respective rows of data depicted in FIG. 5.

FIG. 3A: Diffusion tensor defining three principle diffusivities by their eigenvalues ($\lambda_1$, $\lambda_2$, and $\lambda_3$) and eigenvectors ($v_1$, $v_2$, and $v_3$) with respect to the global coordinate system. FIG. 3B: The diffusion ellipsoid model with axes defined by the diffusion eigenvalues. FIG. 3C: Intersection of the diffusion ellipsoid and plane parallel to the cortical surface. FIG. 3D: Plane defining the cortical surface with normal vector, n, and parallel vector components, r and s. FIG. 3E: Diffusivity perpendicular to the cortical surface, q, in relation to the diffusion ellipsoid and cortical surface. FIG. 3F: Diffusivity measurements parallel to the cortical surface, a and b.

FIG. 4 depicts a table that shows a comparison of clinical variables with electrical conductivity and MRI diffusion. Data presented as F-values/P-values (i.e., the corresponding 2 numbers at each entry) using ANOVA. Comparisons reached a prior statistical significance (P<0.05) for age at surgery and age at seizure onset vs diffusivity parameters both in the parallel and perpendicular directions. Comparison of ratios of diffusivities in the parallel and perpendicular directions with the seizure free duration post-surgery also reached significance at p<0.05 level. Significant values (P<0.05) indicated in Bold.

FIG. 5 depicts a table that shows values of electrical conductivities perpendicular, and parallel, $\sigma_\parallel$, to pia, as well as the DT-MRI values along the corresponding directions.

FIG. 6 depicts a table that shows the linear correlations comparing electrical conductivity ($\sigma$) and DT-MRI (D) measurements. Data presented as R-values/P-values. Significant values (P<0.05) indicated in Bold.

FIG. 7A-FIG. 7H depict graphs demonstrating that positive and significant correlations exist between the ratios of electrical conductivities ($\sigma_\parallel/\sigma\perp$) and DT-MRI values in the perpendicular (FIG. 7A), and parallel (FIG. 7B) directions to the pial surface. Positive and significant correlations also exist between the parallel and perpendicular values of electrical conductivities (FIG. 7C), and those of DT-MRI (FIG. 7D). The slope of best-fitting line in FIG. 3C is 1.38±0.082. No significant correlation is present between the ratios of the electrical conductivities and conductivity parallel to pia (FIG. 7E), the ratios of the DT-MRI values and MRI diffusivity parallel to pia (FIG. 7F), the ratios of the electrical conductivities and the ratios of the DT-MRI (major) (FIG. 7G), and the ratios of the DT-MRI (minor) (FIG. 7H).

Figure 1:
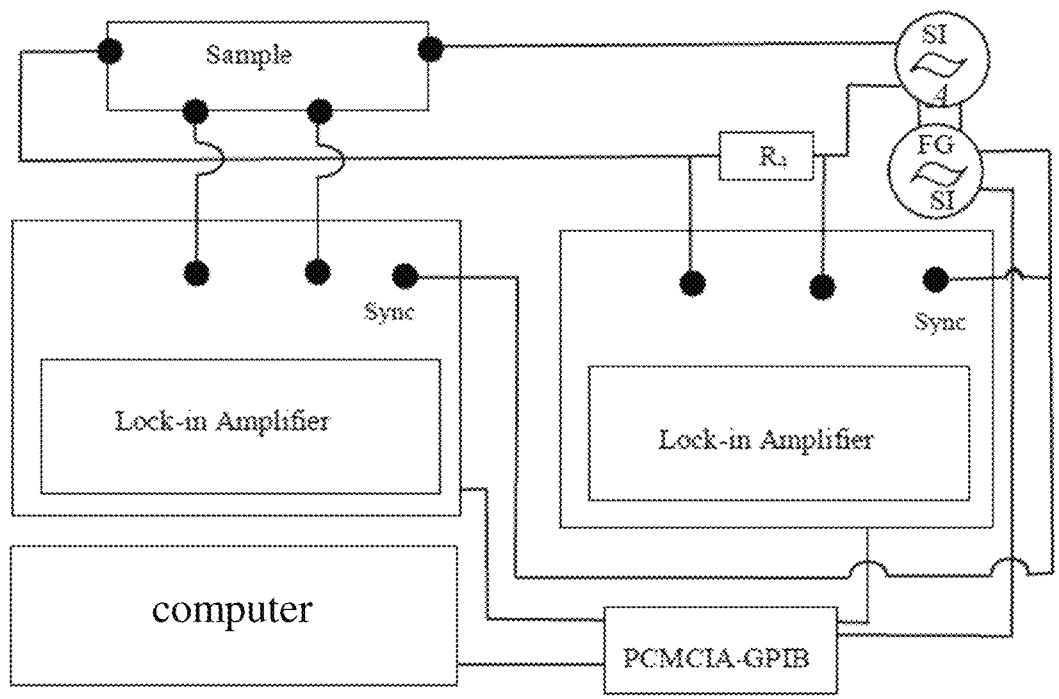
FIG. 1 depicts a schematic diagram of the conductivity measuring instrumentation. A function generator (FG) is used to modulate the current output of a stimulus isolator (SI) through the sample. The potential drops and phase changes are measured through the lock-in amplifiers. The resistor R4 is used to monitor the current and the phase change due to instrumentation. All instrumentation is automated through Lab View software and controlled through a computer, which also records and analyzes all data.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a carrier ion" includes a plurality of such ions and reference to "the processor" includes reference to one or more processors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of generating a conductivity map of an in vivo tissue. The present disclosure provides systems for generating a conductivity map of an in vivo tissue.

Methods of Generating a Conductivity Map

The present disclosure provides methods of generating a conductivity map of an in vivo tissue in a subject. In certain embodiments, the method is a non-invasive method of generating a conductivity map of an in vivo tissue in a subject. Methods that do not involve the puncturing of the skin or an incision, or the introduction of foreign objects or materials into the body of the subject are known as non-invasive methods. For instance, a non-invasive method does not require a surgical procedure to be performed on the subject.

Non-invasive methods may involve performing one or more non-invasive diagnostic procedures on the subject. For example, non-invasive diagnostic procedures may include, but are not limited to, magnetic resonance imaging (MRI), computed tomography (CT), ultrasound, X-ray radiography, electroencephalography (EEG), magnetoencephalography (MEG), electrocardiography (ECG), and combinations thereof. In certain embodiments, the non-invasive methods disclosed herein include MRI. Various types of MRI may be used, such as, but not limited to, diffusion MRI, diffusion tensor MRI (DT-MRI), functional MRI (fMRI), real-time MRI, and the like. In some cases, DT-MRI is used in the presently disclosed methods.

In certain embodiments, the methods are performed in vivo. Methods that are performed in vivo include methods in which an assay is performed on a biological entity that is a whole, living organism, such as an animal (e.g., a mammal; e.g., a non-human mammal (e.g., a non-human primate; a rodent (e.g., a rat; a mouse); a cat; a dog; a horse; etc.); a human), or a plant, as opposed to a part of an organism or a dead organism, or methods performed in vitro, i.e., in a laboratory environment using test tubes, petri dishes, etc. In other instances, the method may be an in vitro method.

In certain embodiments, the method includes measuring a detectable parameter of the tissue in the subject. In some instances, the detectable parameter of the tissue includes a concentration of a carrier ion in the tissue. As such, methods of the present disclosure include measuring a concentration of a carrier ion in a tissue of a subject. In some cases, the concentration of the carrier ion is measured directly in the tissue of the subject. In some cases, the concentration of the carrier ion is measured using a non-invasive diagnostic method, such as MRI. Thus, methods of the present disclosure include measuring the concentration of a carrier ion in a tissue using MRI. The carrier ion may be any carrier ion present in the tissue that is detectable using the presently disclosed methods. In some instances, the carrier ion is sodium, chloride, potassium or calcium. For example, the carrier ion may be sodium ion ($Na^+$). In some cases, the carrier ion is chloride ion ($Cl^-$). In some cases, the carrier ion is potassium ion ($K^+$). In some cases, the carrier ion is calcium ion ($Ca^{2+}$). In certain instances, the concentration of the carrier ion is expressed in mM. In certain instances, the concentration of the carrier ion is expressed in $m^{-3}$. In some embodiments, the MRI can be performed at 0.3 Tesla (T), 1.5 T, 3 T, 7 T, 9 T, or 12 T. In some cases, the MRI is performed at 0.3 T. In some cases, the MRI is performed at 1.5 T. In some cases, the MRI is performed at 3 T. In some cases, the MRI is performed at 7 T. In some cases, the MRI is performed at 9 T. In some cases, the MRI is performed at 12 T.

In some instances, the detectable parameter of the tissue is the water proton diffusivity (D) in the tissue. As such, methods of the present disclosure include measuring the water proton diffusivity in a tissue of a subject. In some cases, the water proton diffusivity is measured using a non-invasive diagnostic method, such as MRI. In some cases, the water proton diffusivity is measured using a non-invasive diagnostic method, such as DT-MRI. Thus, methods of the present disclosure include measuring the concentration of a carrier ion in a tissue using MRI (e.g., using DT-MRI). In certain instances, the water proton diffusivity is expressed in $cm^2/s$, such as $\mu cm^2/s$. In some embodiments, the DT-MRI can be performed at 0.3 T, 1.5 T, 3 T, 7 T, 9 T, or 12 T. In some cases, the DT-MRI is performed at 0.3 T. In some cases, the DT-MRI is performed at 1.5 T. In some cases, the DT-MRI is performed at 3 T. In some cases, the DT-MRI is performed at 7 T. In some cases, the DT-MRI is performed at 9 T. In some cases, the DT-MRI is performed at 12 T.

In some cases, the carrier ion concentration and the water proton diffusivity are measured using a single coil (e.g., radiofrequency receive coil) in the MRI or DT-MRI device. In other cases, the carrier ion concentration and the water proton diffusivity are measured using separate coils in the MRI or DT-MRI device.

In certain embodiments, the detectable parameter of the tissue may include the temperature of the tissue. As such, methods of the present disclosure may include measuring the temperature of a tissue of a subject that is being analyzed. For in vivo methods, the temperature of the tissue may be substantially the same as the normal body temperature of the subject being analyzed. For example, for a human subject, the temperature may be about 37° C. (310 K). For in vitro methods, the temperature of the tissue being analyzed may be substantially the same as the environment surrounding the tissue. In some instances, the temperature of the tissue for an in vitro method may be room temperature, or about 25° C. (300 K). In embodiments where the temperature of the tissue is assumed to be substantially the same as the normal body temperature of the subject or substantially the same as the temperature of the surrounding environment, the method does not need to include a step of measuring the temperature of the tissue. Instead, the method may include inputting temperature data into the system, for example by using a user interface to input the temperature data. In certain cases, the temperature is expressed in degrees Kelvin (K).

The detectable parameters of the tissue being analyzed can be measured in a single target area in the subject (e.g., a uniplex analysis of a target area). By "uniplex" analysis is meant that a single target area is analyzed using the methods and systems disclosed herein. Other embodiments include the multiplex analysis of two or more target areas (e.g., target tissues) in a subject. By "multiplex" analysis is meant that two or more target areas of tissue in a subject may be analyzed using the methods and systems disclosed herein. In some instances, the number of target areas for analysis using multiplex methods and systems as disclosed herein is 2 or more, such as 4 or more, 6 or more, 8 or more, 10 or more, etc., up to 20 or more, e.g., 50 or more, including 100 or more, or 500 or more distinct target areas. In certain embodiments, the methods and systems may be used for the multiplex analysis of 2 to 500 distinct target areas in the subject, such as 2 to 250 distinct target areas, including 2 to 100 distinct target areas, or 2 to 50 distinct target areas, or 2 to 25 distinct target areas, or 2 to 10 distinct target areas. In certain embodiments, 2 or more multiplex assays may be conducted in parallel substantially simultaneously.

Measuring the concentration of the carrier ion in the tissue may generate concentration data. Similarly, measuring the water proton diffusivity in the tissue may generate water proton diffusivity data. In addition, measuring the temperature of the tissue may generate temperature data. In certain instances, the method includes storing the data (e.g., the concentration data and/or the water proton diffusivity data and/or the temperature data) in a data storage of the system. In some cases, the data storage includes a computer readable medium on which the data may be recorded such that the data are accessible and retrievable at a later date by a computer. As such, in addition to storing the data, methods of the present disclosure may include retrieving data from the data storage. In other embodiments, the data (e.g., the concentration data and/or the water proton diffusivity data and/or the temperature data) may be obtained and then analyzed in real-time. By "real-time" is meant that the acquired data are analyzed by the system (e.g., a processor) immediately after the measurement data are acquired.

In certain embodiments, the method further includes analyzing the measured concentration of the carrier ion and analyzing the measured water proton diffusivity to determine a parameter associated with the analyzed tissue. In some cases, the parameter to be determined is a conductivity associated with the analyzed tissue. Stated another way, methods of the present disclosure include determining the conductivity of a target tissue in a subject based on the concentration of the carrier ion and the water proton diffusivity of the target tissue. The conductivity may be determined at one or more target areas in the subject. In some cases, the method includes determining an average conductivity for a target tissue area. By average is meant the arithmetic mean. In some embodiments, the method includes determining a directional component of the conductivity. For example, the method may include determining the conductivity in a certain direction with respect to a surface of the analyzed tissue. In some cases, the method includes determining the conductivity in a direction perpendicular to a surface of the analyzed tissue. In some cases, the method includes determining the conductivity in a direction parallel to a surface of the analyzed tissue.

In certain instances, the method includes generating a conductivity map of the tissue. The conductivity map of the tissue may be a 2-dimensional or 3-dimensional representation of empirically determined conductivity values associated with the analyzed tissue. In some instances, the conductivity map is constructed by determining the conductivity at a plurality of target areas in a tissue of the subject and combining the determined conductivity values into a conductivity map of the tissue.

As described above, embodiments of the presently disclosed methods include using the measured carrier ion concentration and the measured water proton diffusivity to determine a conductivity value associated with a tissue and/or generate a conductivity map of the tissue. In certain embodiments, the method includes using an equation to determine the conductivity values, and thus generate the conductivity map of the tissue. For example, the measured carrier ion concentration and the measured water proton diffusivity may be used in the following equation:

$$\sigma = (D\, n\, q^2)/kT$$

where $\sigma$ is conductivity, D is the water proton diffusivity, n is the concentration of the carrier ion, q is the charge of the carrier ion, k is Boltzmann constant, and T is temperature in degrees Kelvin.

In certain embodiments, $\sigma$ is conductivity, where the conductivity is expressed in siemens per meter (S/m), such as mS/m.

In certain embodiments, D is the water proton diffusivity, where D is expressed in $cm^2/s$, such as $\mu cm^2/s$.

In certain embodiments, n is the concentration of the carrier ion, where the concentration is expressed in $m^{-3}$.

In certain embodiments, q is the charge of the carrier ion. The q of the carrier ion may be calculated by multiplying the fundamental physical constant for elementary charge by the electrical charge of the carrier ion. The elementary charge physical constant is equal to $1.6 \times 10^{-19}$ coulomb (C). The electrical charge of the carrier ion is an integer equal to the difference between the total number of protons and the total number of electrons in the carrier ion. For example, for a sodium carrier ion ($Na^+$), the electrical charge is 1.

In certain embodiments, k is Boltzmann constant, which is equal to $1.381 \times 10^{-23}$ J/K.

In certain embodiments, T is temperature in degrees Kelvin (K), e.g., the temperature of the tissue being analyzed, such as, for example, the normal body temperature of the subject for in vivo assays or the temperature of the environment surrounding the tissue being analyzed for in vitro assays.

In certain embodiments, the method includes generating one or more frequencies, gradients and/or pulses for measuring the concentration of the carrier ion in the tissue.

The frequencies, gradients and/or pulses may be generated by one or more electronic devices included in the MRI device. For example, the electronic devices may include one or more magnets, such as electromagnets.

In some instances, the method of the present disclosure is performed once. In other cases, the method is performed two or more times. In some cases, the method is performed several times over a period of time, e.g., the method includes chronically determining the conductivity of the tissue. In some cases, the method may be performed periodically over an extended period of time, such as 1 day or more, 2 days or more, 3 days or more, 4 days or more, 5 days or more, 6 days or more, 7 days or more, 8 days or more, 9 days or more, 10 days or more, such as, for example, 1 week or more, 2 weeks or more, 3 weeks or more, 1 month or more, 2 months or more, 3 months or more, 4 months or more, 5 months or more, 6 months or more, 7 months or more, 8 months or more, 9 months or more, 10 months or more, 11 months or more, 1 year or more, or ever longer periods of time.

In some cases, the individual is a human. In some cases, the individual is a non-human primate. In some cases, the individual is a rodent (e.g., a rat, a mouse, etc.). The target tissue may be an in vivo neuronal tissue, a tissue slice preparation, a nerve fiber bundle, a neuromuscular junction, etc. The in vivo neuronal tissue may be neuronal tissue of an animal that is anesthetized or non-anesthetized, and is restrained or non-restrained. The target tissue of interest may include, but is not limited to, the neocortex, the hypothalamus, entorhinal and hippocampal formation cortex, mammillary bodies, septum, bed nucleus of stria terminalis, dorsal and ventral striatum, thalamus, amygdala, accumbens, brainstem, subcortical structures in general, muscle, spinal cord, cardiac (heart) tissue, etc.

In some cases, the tissue is brain tissue. In other cases, the tissue is heart tissue. For example, in embodiments where the tissue being analyzed is brain tissue, the present disclosure provides a non-invasive method of generating a conductivity map of the brain of a living individual. As described herein, the method includes measuring the concentration of a carrier ion in a brain tissue of the individual using MRI and measuring the water proton diffusivity (D) in the brain tissue using DT-MRI. The method may also include generating a conductivity map of the brain tissue, using the measured carrier ion concentration and the measured water proton diffusivity. As described herein, the method may include generating the conductivity map of the tissue using the formula:

$$\sigma = (D\, n\, q^2)/kT$$

where σ is conductivity, D is the water proton diffusivity, n is the concentration of the carrier ion, q is the charge of the carrier ion, k is Boltzmann constant, and T is temperature in degrees Kelvin (K).

Methods of the present disclosure for generating a conductivity map of an in vivo tissue may include determining the conductivity of the target tissue. In some instances, the target tissue includes normal tissue. In other instances, the target tissue includes abnormal tissue. In some embodiments, the methods of the present disclosure include determining the location of abnormal tissue (e.g., pathological tissue; diseased tissue) in a subject, where the abnormal tissue has a conductivity that differs from normal (non-diseased) tissue. For example, a method of the present disclosure for generating a conductivity map of an in vivo tissue may include determining the location of epileptic lesions, a tumor, damaged tissue (e.g., damaged tissue resulting from ischemia caused by stroke or myocardial ischemia), abnormal tissue caused by Alzheimer's disease, and/or abnormal tissue caused by Parkinson's disease, and the like.

Thus, the present disclosure provides a non-invasive method of localizing a diseased tissue in a living individual. The method involves generating a conductivity map of the target tissue in the living individual, as described above, and, based on the conductivity map, localizing an area of abnormal conductivity. In some cases, the area of abnormal conductivity is an indication of abnormal (e.g., diseased) tissue. In some cases, the diseased tissue is a tumor. In some cases, the diseased tissue is ischemic tissue. In some cases, the diseased tissue is an epileptic lesion. In some cases, the diseased tissue comprises neurofibrillary tangles and/or amyloid plaques.

As such, methods of the present disclosure may include diagnosing an individual for a disease or condition based on the conductivity map. For instance, based on the generated conductivity map, methods of the present disclosure may include diagnosing the individual for epilepsy, a tumor, stroke, myocardial ischemia, Alzheimer's disease, or Parkinson's disease.

In some cases, localization of a diseased tissue (and/or diagnosing the individual for a disease or condition) is followed by treatment. For example, where the diseased tissue is a tumor, the method may include treating the individual by resection of the diseased tissue. For instance, where the diseased tissue is an epileptic lesion, the method may include treating the individual by lesionectomy. In some instances, treating the individual may include administering a therapeutically effective amount of a drug to treat the disease or condition. For example, where the diseased tissue is a tumor, an epileptic lesion, damaged tissue resulting from stroke or myocardial ischemia, Alzheimer's disease or Parkinson's disease, the method may include administering a therapeutically effective amount of a drug to treat the disease or condition.

"Pharmaceutically effective amount" and "therapeutically effective amount" refer to an amount of a compound sufficient to treat a specified disorder or disease or one or more of its symptoms and/or to prevent the occurrence of the disease or disorder. For example, in reference to tumors, a pharmaceutically or therapeutically effective amount may include an amount sufficient to, among other things, cause the tumor to shrink or decrease the growth rate of the tumor.

In certain embodiments, a method of the present disclosure for generating a conductivity map of an in vivo tissue includes providing guidance for placement of deep brain stimulation (DBS) electrodes. A conductivity map, generated as disclosed herein, allows for more precise placement of DBS electrodes. DBS is used in the treatment of a variety of disorders, including, e.g., Parkinson's disease, Alzheimer's disease, depression, dystonia, chronic pain, and epilepsy. Thus, the present disclosure provides methods of treatment, comprising: a) generating a conductivity map of a brain of an individual, as described above; and b) placing DBS electrodes in the brain, using information from the conductivity map, to place the electrodes in or near a desired target brain area (e.g., a brain area exhibiting abnormal conductivity).

In some embodiments, methods of the present disclosure include methods for identifying a treatment, e.g., a therapeutic treatment, with a desired activity on a brain tissue (e.g., a group of neurons). If the desired outcome is known, then the method may include screening for treatments, including, but not limited to, pharmacological agents (drugs), nonchemical based therapeutic treatment, behavioral treatment, electrical, magnetic, or optical based neural-modulation treatment, etc., that will bring about the desired neuronal activity pattern. The screening may be performed in any suitable animal model, either normal, or a model for a neurological disorder, such as, but not limited to, Alzheimer's disease, Parkinson's disease, mild cognitive impairment, other dementias, and Down's Syndrome, as well as schizophrenia, autism, mood disorders, affective disorders, anxiety, personality/developmental disorders, and the like.

In some embodiments, the method includes treating a condition or disorder, such as a neurological or psychiatric condition using deep brain stimulation (DBS) and/or opto-genetic control. As real time activity of neurons can be monitored as described herein using the present methods and systems, a controller or processor may be configured to modulate the activity of neurons based on the generated conductivity map in such a way as to treat or reduce symptoms of the condition or disorder, at the behavioral and/or physiological levels.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The terms "subject," "individual," "patient," and the like, are used interchangeably herein to refer to an animal undergoing a method of the present disclosure, or on whom a method of the present disclosure is to be performed. Suitable animals include mammals, e.g., a non-human mammal (e.g., a non-human primate; a rodent (e.g., a rat; a mouse); a cat; a dog; a horse; etc.); a human; etc. In some cases, the individual is a human. In some cases, the individual is a non-human mammal. In some cases, the individual is a non-human primate. In some cases, the individual is a rodent (e.g., a mouse; a rat). In some cases, the individual is a feline, e.g., a cat. In some cases, the individual is a canine, e.g., a dog. In some cases, the individual is an ungulate.

Systems

The present disclosure provides a system for performing the methods disclosed herein. In certain embodiments, the system is configured for generating a conductivity map of an in vivo tissue. The system may include a magnetic resonance imaging (MRI) device. The MRI device may be configured to measure a concentration of a carrier ion in the tissue. In some cases, the MRI device is also configured to measure the water proton diffusivity (D) in the tissue. For example, the MRI device may include a coil (e.g., a transceiver coil) for measuring the concentration of the carrier ion in the tissue. In some cases, the MRI device includes a coil (e.g., a transceiver coil) for measuring the water proton diffusivity in the tissue. In some embodiments, the coil for measuring the concentration of the carrier ion and the coil for measuring the water proton diffusivity are the same coil. As such, in these embodiments, the MRI device includes a single coil for measuring the concentration of the carrier ion and the water proton diffusivity in the tissue. In other embodiments, the coil for measuring the concentration of the carrier ion and the coil for measuring the water proton diffusivity are different coils. Thus, in these embodiments, the MRI device may include a first coil for measuring the concentration of the carrier ion and a second coil for measuring the water proton diffusivity.

Embodiments of the system also include a processor. The processor may be configured to execute programming (i.e., instructions) stored in the system (e.g., stored in a non-transient memory of the system), where execution of the programming by the processor causes the processor to generate a conductivity map of the tissue based on measurements from the MRI device. In some cases, the processor is configured to execute programming (i.e., instructions) that causes the processor to generate a conductivity map of the tissue based on the measured concentration of the carrier ion and the measured water proton diffusivity as described herein. For example, the processor may be configured to execute programming (i.e., instructions) that cause the processor to generate a conductivity map of the tissue using the formula:

$$\sigma = (D\ n\ q^2)/kT$$

where $\sigma$ is conductivity, D is the water proton diffusivity, n is the concentration of the carrier ion, q is the charge of the carrier ion, k is Boltzmann constant, and T is temperature in degrees Kelvin, as described herein.

In certain embodiments, the system includes one or more electronic devices configured to generate one or more frequencies, gradients and/or pulses for measuring the concentration of the carrier ion in the tissue. The frequencies, gradients and/or pulses may be generated by one or more electronic devices included in the MRI device. For example, the electronic devices may include one or more magnets, such as electromagnets.

The system can further include a data storage that is configured to store data. The data storage may be operably connected to the MRI device and/or the processor. For example, in some cases, the data storage is configured to store data measured by the MRI device, such as carrier ion concentration data, water proton diffusivity data, temperature data, and the like. In some instances, the data storage is configured to store data, such as conductivity map data that is generated by the processor.

The system can further include a user interface and a data connector that transmits data from the processor to the user interface. The user interface may include any convenient user interface, such as, for example, a display, a touchscreen display, a keypad, a keyboard, a mouse, combinations thereof, and the like. In some instances, the user interface is configured to accept user inputs from a user of the system. For instance, the user interface may be configured to accept user inputs, such as, but not limited to, commands to begin or end an assay, commands to measure the concentration of a carrier ion in a particular target tissue area, commands to measure the water proton diffusivity in a particular target tissue area, commands to generate a conductivity map of the target tissue, user inputs for naming an assay and/or data file(s), etc. The user interface may be operably connected to the MRI device and/or the processor, such as through a data connector that transmits data between the processor and the user interface.

In certain embodiments, the system can be used to non-invasively generate a conductivity map of an in vivo tissue. Based on the generated conductivity map, the system may be configured to identify abnormal tissue within a target tissue in a living individual, as described above. As such, the system may be configured for localization of an abnormal tissue in an individual, where the abnormal tissue has a conductivity that differs from normal (non-diseased) tissue.

Utility

Methods and systems of the present disclosure for generating a conductivity map of an in vivo tissue are useful for determining the conductivity of the target tissue non-invasively. In some instances, the target tissue includes normal tissue. In other instances, the target tissue includes abnormal tissue. In some embodiments, the methods of the present disclosure are useful for localization of abnormal tissue (e.g., pathological tissue; diseased tissue), where the abnormal tissue has a conductivity that differs from normal (non-diseased) tissue. For example, the subject methods and systems are useful for localization of epileptic lesions, for localization of a tumor, for localization of damaged tissue (e.g., damaged tissue resulting from ischemia caused by stroke or myocardial ischemia), localization of abnormal tissue caused by Alzheimer's disease, and localization of abnormal tissue caused by Parkinson's disease.

Thus, methods and systems of the present disclosure are useful for non-invasively localizing a diseased tissue in a living individual. The methods and systems are useful for generating a conductivity map of the target tissue in the living individual, as described above, and, based on the conductivity map, localizing an area of abnormal conductivity. In some cases, the methods and systems are useful for identifying and localizing an area of abnormal conductivity, such as a tumor, ischemic tissue, epileptic lesions, neurofibrillary tangles and/or amyloid plaques.

In some embodiments, the subject methods and systems find use in screening in vitro and/or in vivo animal models of disease for tissues (e.g., brain tissue or neurons) that are diagnostic of or causative for neuropsychiatric disease. In some embodiments, the present methods and systems find use in diagnosis of neuropsychiatric diseases of interest, which may include disorders of mood and affect, anxiety, psychosis, personality, etc. The animal model may be any suitable model, including, but not limited to, rodents, cats, dogs, monkeys, and non-human primates. Perturbations used to model a neuropsychiatric disease include genetic models of neurological or psychiatric disease, such as autism; chronically induced models as with kainate or pilocarpine-induced epilepsy or chronic stress-induced depression; and acutely induced models as with hallucinogens or psychotogenic agents such as ketamine or phencyclidine (PCP). By comparing the difference in conductivity between neurons in normal target tissue and neurons in abnormal target tissue, neural correlates of the neuropsychiatric disorder may be identified. Embodiments of the subject methods and systems may then allow identification of causative abnormal neuronal conductivity patterns for a particular neuropsychiatric disorder. As such, in some cases, the methods and systems of the present disclosure may potentially provide novel treatment targets. Thus, in some embodiments, the present methods and systems find use in diagnostic methods for neuropsychiatric diseases, e.g., where the diagnosis is carried out on a human or non-human mammalian subject.

In some embodiments, the present methods and systems find use in identifying a treatment, e.g., a therapeutic treatment, with a desired activity on a target tissue (e.g., a brain tissue, such as a group of neurons). If the desired outcome is known, then the present system and method may be used to screen for treatments, including, but not limited to, pharmacological agents, nonchemical based therapeutic treatment; behavioral treatment; electrical, magnetic, or optical based neural-modulation treatment; etc., that will bring about the desired neuronal activity pattern. The screening may be performed in any suitable animal model, either normal, or a model for a neurological disorder, such as Alzheimer's and Parkinson's disease, mild cognitive impairment, other dementias, and Down's Syndrome, as well as schizophrenia, autism, mood, affective, anxiety, and personality/developmental disorders, and the like.

In some embodiments, the present methods and systems find use in the treatment of a condition or disorder, such as a neurological or psychiatric condition. As real time activity of neurons can be monitored using the present methods and systems, a controller or processor may be configured to provide a treatment that modulates the activity of neurons in response to the generated conductivity map in such a way as to treat or reduce symptoms of the condition or disorder, at the behavioral and/or physiological levels.

For example, in certain embodiments, methods and systems of the present disclosure are useful for providing guidance for placement of deep brain stimulation (DBS) electrodes. A conductivity map, generated as disclosed herein, allows for more precise placement of DBS electrodes. DBS is used in the treatment of a variety of disorders, including, e.g., Parkinson's disease, Alzheimer's disease, depression, dystonia, chronic pain, and epilepsy. Thus, the present disclosure provides methods and systems useful for treatments involving DBS treatment. For instance, the methods and systems of the present disclosure are useful for generating a conductivity map of a brain of an individual, as described above, which guides the placement of DBS electrodes in the brain using information from the conductivity map to place the electrodes in or near a desired target brain area (e.g., a brain area exhibiting abnormal conductivity).

Computer Related Embodiments

A variety of computer-related embodiments are also provided. Specifically, the data analysis methods described herein may be performed using a computer, e.g., a processor. Accordingly, provided is a computer-based system for analyzing data produced using the above methods and systems in order to provide qualitative and/or quantitative analysis of a target area of interest in a subject.

In certain embodiments, the methods are coded onto a computer-readable medium in the form of "programming" or "instructions", where the term "computer-readable medium" as used herein refers to any storage or transmission medium that participates in providing instructions and/or data to a computer for execution and/or processing. Examples of storage media include CD-ROM, DVD-ROM, BD-ROM, a hard disk drive, a ROM or integrated circuit, a magneto-optical disk, a solid-state memory device, a computer readable flash memory, and the like, whether or not such devices are internal or external to the computer. A file containing information may be "stored" on computer readable medium, where "storing" means recording information such that it is accessible and retrievable at a later date by a computer or processor. Examples of media include, but are not limited to, non-transitory media, e.g., physical media in which the programming is associated with, such as recorded onto or stored by, a physical structure. Non-transitory media for storing computer programming does not include electronic signals in transit via a wireless protocol.

In certain embodiments, computer programming may include instructions for directing a computer to perform one or more assay steps as disclosed herein. For example, the computer programming may include instructions for directing a computer to detect and/or analyze signals acquired by the devices disclosed herein (e.g., MRI and/or DT-MRI devices). In certain embodiments, the computer programming includes instructions for directing a computer to analyze the acquired signals qualitatively and/or quantitatively. Qualitative determination includes determinations in which a simple yes/no result is provided to a user with respect to the presence or absence of a detectable signal. Quantitative determination includes both semi-quantitative determinations in which a rough scale result, e.g., low, medium, high, is provided to a user regarding the detectable signal and fine scale results in which an exact measurement of the detectable signal is provided to a user (e.g., a quantitative measurement of carrier ion concentration and/or water proton diffusivity in a target area of interest).

With respect to computer readable media, "permanent memory" refers to memory that is permanent, i.e., non-volatile memory. Permanent memory is not erased by termination of the electrical supply to a computer or processor. Computer hard-drive, CD-ROM, DVD-ROM, BD-ROM, solid state memory, flash memory, and holographic memory are all examples of permanent memory. Random Access Memory (RAM) is an example of non-permanent memory. A file in permanent memory may be editable and re-writable. Similarly, a file in non-permanent memory may be editable and re-writable.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

The following materials and methods were used in Examples 1-4 described below.

Study Population

This study was performed at UCLA's Pediatric Epilepsy Program that had combined electrical conductivity studies and MRI diffusion tensor imaging for use in this study (n=24). The pre-surgical clinical protocols and evaluation process along with methods describing collection of clinical epilepsy variables, and post-surgery seizure outcome are described in Akhtari et al., *Brain Topogr.* 2006, 18(4):281-290; Akhtari et al., *Brain Topogr.* 2010, 23(3):292-300; Hauptman et al., *Epilepsia.* 2012, 53 Suppl 4:98-104, the disclosures of each of which are incorporated herein by reference. Seizure etiology categories were based on MRI and histopathology, and catalogued into cases of cortical dysplasia (CD; n=13) and non-CD cases (n=11). Inclusion criteria were if the planned cortical resection was large enough that additional brain tissue beyond what was needed for diagnostic histopathology would be available for research. Except for the size of the operation there were no exclusion criteria.

Electrical Conductivity

The electrical conductivities of the freshly excised brain tissues were obtained using the four-electrode method (Schwann, *Ann N Y Acad Sci.* 1968, 148(1):191-209) as described previously (Akhtari et al., *Brain Topogr.* 2006, 18(4):281-290; Akhtari et al., *Brain Topogr.* 2010, 23(3): 292-300). In brief, freshly excised brain tissue samples, approximately 1 cm$^3$ in volume, were inserted inside a plastic cylindrical holder. Coated silver wires were attached to the one side of indium foils (area=1.2 cm$^2$) which were attached to the rubber tips of plungers. The tissue axis perpendicular to the pial surface was placed along the long axis of the holder. Two coated platinum wires (4 mm exposed) were inserted inside the brain tissue through holes (~0.5 mm diameters, 5 mm apart) on the holder. Frequency modulated (6-1005 Hz) constant current (60 µA) was passed through the brain tissue through the indium electrodes and the resulting tissue potential drop and phase was measured across the platinum wires through a lock-in amplifier at each frequency step. The circuit current and phase were monitored through a second lock-in amplifier (FIG. 1). The tissue conductivity was calculated using ohm's law, J=σE, where σ is the conductivity tensor representing the conductivities in the directions defined by the ratio $$\frac{J}{E},$$

J is the current density (encompassing the entire sample in the prescribed direction), and E is the electric field (Akhtari et al., *Brain Topogr.* 2006, 18(4):281-290; Akhtari et al., *Brain Topogr.* 2010, 23(3):292-300; Okada et al., *J Neurophysiol.* 1994, 72(2):742-753; Nicholson and Freeman, *J Neurophysiol.* 1975, 38(2):356-368). The lower bound of uncertainty (e.g., due to instrumentation) in conductivity measurements was calculated using:

$$\delta\sigma = \left[\left(\left(\frac{\partial\sigma}{\partial l}\right)\delta l\right)^2 + \left(\left(\frac{\partial\sigma}{\partial A}\right)\delta A\right)^2 + (\delta R)^2 + (\delta S)^2\right]^{\frac{1}{2}}$$

where l≡inter-electrode distance, A≡electrode area, δR≡uncertainty in potential measurement, and δS≡uncertainty in current measurements, with the latter two adjusted for conformity of units (Beers, *Introduction to the theory of error. Second Edition, Addison-Wesley Publishing (London).* 1953). It was noted that δl is systematic within the repeated measurements of one sample, while δA is systematic within all measurements in all samples. These uncertainties were used to determine if the electrical conductivities perpendicular and parallel to the pial surface were statistically different indicating isotropy or anisotropy, using the chi-squared test.

The following SI units and definitions are used:

$$\text{conductance} = \frac{1}{\text{resistance}(R)}, \text{unit} \equiv \text{siemens}(S) = \frac{1}{\text{ohm}(\Omega)}$$

$$\text{conductivity}(\sigma) = \frac{1}{\text{resistivity}(\rho)}, \text{unit} \equiv \frac{S}{\text{meter}(m)}$$

The response of the medium was assumed to be linear and constant in the limit relevant to electromagnetic source localization (i.e., the imaginary part of permittivity can be ignored; Stinstra and Peters, *Med. Biol. Eng. Comput.* 1998, 36:711-716; Stock, *IEEE Trans. Biomed. Eng.* 1987, BME-34:289-296; Cuffin et al., *Ann. Neurol.* 1991, 29:132-138) consistent with the lack of remarkable phase angle changes in conductivity measurements (Akhtari et al., *Brain Topogr.* 2000, 13(1):29-42; Akhtari et al., *Brain Topogr.* 2003, 16(1): 39-55; Akhtari et al., *Brain Topogr.* 2006, 18(4):281-290; Akhtari et al., *Brain Topogr.* 2010, 23(3):292-300).

Diffusion Tensor Magnetic Resonance Imaging

Figure 3A:
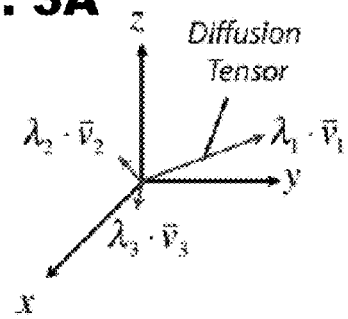
FIG. 3A-FIG. 3F depict various models and equations.

DT-MRI data were collected on a Siemens 1.5T (Avanto or Sonata) or 3T MR system (Trio or Verio) using either 6 or 12 directions. DT-MR images were collected with b=0 s/mm$^2$ and either b=600, 700, or 1200 s/mm$^2$ using diffusion gradient amplitude (G)=20-30 mT/m, diffusion encoding time (δ)=15-22 ms, diffusion mixing time (Δ)=40-70 ms, a repetition time (TR)=4.5-10 sec, echo time (TE)=78-129 ms, slice thickness of 2-5 mm, a field of view from 18 cm$^2$ to 26 cm$^2$, a matrix size of 128×128, and from 1-4 averages. (FIG. 2) The 3×3 diffusion tensor was calculated using FSL's FDT toolbox (FMRIB; Oxford, UK). The eigenvalues ($\lambda_1$, $\lambda_2$, $\lambda_3$), ranked by their relative magnitude where $\lambda_1$ was the largest, and eigenvectors ($v_1$, $v_2$, $v_3$) corresponding to the orientation of these eigenvalues were estimated from the diffusion tensor (FIG. 3A).

Alignment of DT-MRI to Cortical Surface Orientation

The conductivity parameters were measured in directions parallel and perpendicular to the cortical surface. The DTI parameters, computed from pre-surgical DT-MR images and in the same tissues used for conductivity measurements, showed the principal directions of tissue water proton diffusion in these tissues. These diffusion directions were determined inherently by the tissues and were measured in local voxels whose coordinates were defined in the MRI coordinate system. In DT-MRI, diffusivity (D) within a voxel was represented by the surface of an oblate ellipsoid contained within the individual voxel. This ellipsoid was defined by the major and minor axes of diffusivity. The magnitude of a vector from the center of this ellipsoid to any point on its surface represented diffusivity in that direction. Therefore, to obtain the diffusivities in the directions in which the conductivities were measured the following operation was performed: a centered plane, parallel to the cortical surface for the intended region of interest (ROI), was defined within individual ellipsoids. The intercept of the ellipsoid and the normal to this plane defined the diffusivity in the direction normal to the cortical surface (D⊥). The maximum and minimum intercept distances with the ellipsoid parallel to this plane defined the diffusivities parallel to the ROI cortical surface ($D_{\|major}$ and $D_{\|minor}$). Since each ROI contained many voxels, this operation was performed on each voxel contained within ROI. Next, the average and standard deviations of these diffusivities were calculated and used in comparison with the measured conductivities. The analytical treatment of this approach was an extension of methodology employed by, e.g., Klein, *Applied Mathematics*. 2012, 3:1634-1640; Tauxe et al., *J Geophysical Res.* 1990, 95(B4):4391-4404; Stejskal, *J Chem. Phys.* 1965, 43(10):3597-3603; Jost, *Diffusion in Solids, Liquids and Gases*. Academic Press, New York. 1952, and is provided below.

The resected gyri ROI were manually delineated on pre-operative T2 weighted scans by the attending neuroradiologist. The direction that the gyms was aligned along its apex was visually determined in the MRI coordinate system and recorded. The anatomical T2-weighted scan was then registered to the b=0 s/mm² image DT-MRI dataset using FLIRT, FSL's linear registration tool, aligning the ROI in the process. The diffusion eigenvalues and eigenvectors for every voxel in the ROI were exported and evaluated using MATLAB (Mathworks Inc, USA).

The diffusion tensor for each image voxel can be described in terms of a "diffusion ellipsoid model" that describes the three axes of the ellipsoid in terms of the diffusion eigenvalues (FIG. 3B):

$$\frac{x'^2}{\lambda_1^2} + \frac{y'^2}{\lambda_2^2} + \frac{z'^2}{\lambda_3^2} = 1$$

Figure 3D:
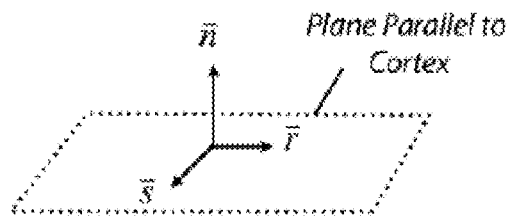
Figure 3B:
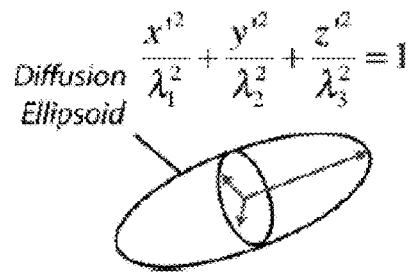

Here, x', y', and z' are a new coordinate system aligned with the axes of the diffusion ellipsoid described by the direction of the eigenvectors, $\vec{v}_1$, $\vec{v}_2$ and $\vec{v}_3$. Next, the plane defined parallel to the cortical surface was identified and a vector normal to the plane, $\vec{n}=(n_{x'}, n_{y'}, n_{z'})^T$, and vectors parallel to the plane, $\vec{r}$ and $\vec{s}$ were defined (FIG. 3D). The diffusivity measured parallel and perpendicular to the cortical surface was then defined according to the intersection of this diffusion ellipsoid with the plane defining the cortical surface, localized to the center of the ellipsoid (FIG. 3C).

Figure 3E:
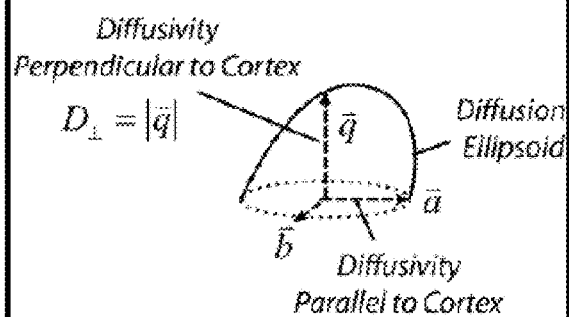
Figure 3C:
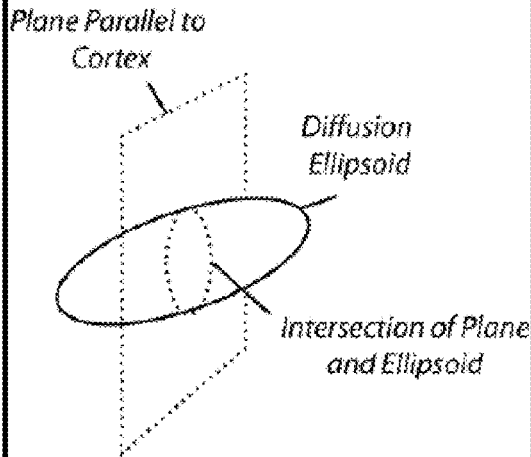

The diffusion perpendicular to the cortical surface, D⊥, can be defined by the point $\vec{q}=(q_{x'}, q_{y'}, q_{z'})^T$ n the diffusion ellipsoid at which the vector normal to the plane, $\vec{n}$, intersects with the ellipsoid. This was determined by expressing the line in parametric form, then substituting into the diffusion ellipsoid equation and solving for $|\vec{q}|$:

$$\frac{(|\vec{q}| \cdot n_{x'})^2}{\lambda_1^2} + \frac{(|\vec{q}| \cdot n_{y'})^2}{\lambda_2^2} + \frac{(|\vec{q}| \cdot n_{z'})^2}{\lambda_3^2} = 1$$

where $D\perp = |\vec{q}|$ is the water diffusivity measured perpendicular to the cortical surface (FIG. 3E).

Vectors $\vec{r}$ and $\vec{s}$ define a plane with normal vector $\vec{n}$ parallel to the cortical surface, and then the intersection of the diffusion ellipsoid and this plane resulted in an ellipse with major and minor axes defined by $\vec{a}$ and $\vec{b}$, which describe diffusivity parallel to the cortical surface (Klein, *Applied Mathematics*. 2012, 3:1634-1640). If the intersection of the diffusion ellipsoid and this surface contains an interior point $\vec{h}=(h_{x'}, h_{y'}, h_{z'})^T$, the plane can be described in parametric form as $\vec{g}=\vec{h}+t\vec{r}+u\vec{s}$ where $\vec{g}=(g_{x'}, g_{y'}, g_{z'})^T$. Substitution results in the equation for the intersection ellipse defined by (FIG. 3F):

$$\frac{t^2}{|\vec{a}|^2} + \frac{u^2}{|\vec{b}|^2} = 1$$

where the semi-axes are defined as:

$$|\vec{a}| = \sqrt{\frac{1-d}{\frac{r_{x'}^2}{\lambda_1^2} + \frac{r_{y'}^2}{\lambda_2^2} + \frac{r_{z'}^2}{\lambda_3^2}}},$$

$$|\vec{b}| = \sqrt{\frac{1-d}{\frac{s_{x'}^2}{\lambda_1^2} + \frac{s_{y'}^2}{\lambda_2^2} + \frac{s_{z'}^2}{\lambda_3^2}}},$$

and $$d = \left[\frac{h_{x'}^2}{\lambda_1^2} + \frac{h_{y'}^2}{\lambda_2^2} + \frac{h_{z'}^2}{\lambda_3^2}\right] - \left(\frac{\left[\frac{h_{x'} r_{x'}}{\lambda_1^2} + \frac{h_{y'} r_{y'}}{\lambda_2^2} + \frac{h_{z'} r_{z'}}{\lambda_3^2}\right]^2}{\frac{r_{x'}^2}{\lambda_1^2} + \frac{r_{y'}^2}{\lambda_2^2} + \frac{r_{z'}^2}{\lambda_3^2}}\right) - \left(\frac{\left[\frac{h_{x'} s_{x'}}{\lambda_1^2} + \frac{h_{y'} s_{y'}}{\lambda_2^2} + \frac{h_{z'} s_{z'}}{\lambda_3^2}\right]^2}{\frac{s_{x'}^2}{\lambda_1^2} + \frac{s_{y'}^2}{\lambda_2^2} + \frac{s_{z'}^2}{\lambda_3^2}}\right)$$

Figure 3F:
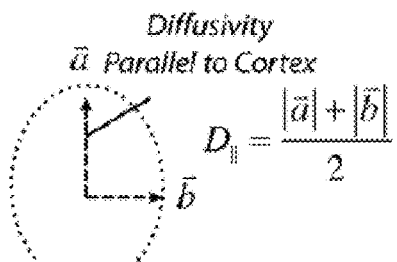

The diffusivity measured parallel to the cortical surface was estimated as the average of the diffusion measurements along vectors $\vec{r}$ and $\vec{s}$ (FIG. 3F).

$$D_p = \frac{|\vec{a}| + |\vec{b}|}{2}$$

Diffusion measurements from each ROI were evaluated using column statistics in Prism statistical software (Prism Software Corp. CA, USA.), producing median, mean, skew, and standard deviation estimates.

Statistical Analysis

Clinical variables, electrical conductivity, and DT-MRI measurements were analyzed using StatView 5 (SAS Institute, Inc. Cary, N.C.). Statistical tests included ANOVA followed by Tukey post-hoc comparison, regression analysis, and Chi-square tests when appropriate. All tests were two-tailed. The threshold for significance was set a priori at p<0.05 for the comparison of conductivity and diffusion measures with clinical variables (FIG. 4), as well as the comparison of electrical conductivity with diffusion variables (FIG. 5). Comprehensive comparisons where made between the magnitudes and ratios of conductivity and the corresponding proton diffusion values. Correlations that achieved significance are reported.

Example 1

Cohort Description and Clinical Comparisons

There were 24 cases used in this study comparing electrical conductivity, MRI diffusion measures, and clinical variables. Clinical epilepsy variables were similar to other cohorts reported by our group (Baca et al., *Neurology.* 2013, 80(13):1231-1239). Mean (±SD; years) age at seizure onset was 3.4±2.3, age at surgery was 5.8±5.2, and epilepsy duration was 3.5±3.0. There were 12(50%) females, 11(46%) left sided resections, and 14 (58%) patients had a history of infantile spasms. Etiology was defined as cortical dysplasia (CD; 54%; CDII, n=5; CDI, n=4; tuberous sclerosis complex, n=3, and hemimegalencephaly, n=1) and non-CD etiologies (perinatal ischemia/infarct, n=4; history of encephalitis, n=3, Rasmussen encephalitis, n=2, and low grade glioma, n=2). Surgery consisted of 14 (58%) cases of cerebral hemispherectomy, five (21%) multi-lobar resections, and five (21%) cases of lobar/focal resections. Pre-surgery, 20 patients had more than a seizure per day, and the other four were having weekly seizures. Post-surgery seizure outcomes were available on 22 (92%) patients, and 19 (86%) were seizure free.

Comparison of clinical variables with electrical conductivity perpendicular and parallel to the pial surface, MRI diffusion perpendicular and parallel to the pial surface, and the ratio of the electrical and diffusion measures showed correlations (p<0.05) for age at surgery and age at seizure onset. This was found with diffusivity parameters both in the parallel and perpendicular directions; and the ratios of diffusivities in the parallel and perpendicular directions compared with the seizure free duration post-surgery (FIG. 6).

Example 2

Electrical Conductivity Values

The values of the electrical conductivity in directions perpendicular ($\sigma\perp$) and parallel ($\sigma_\parallel$) to the cortical surface are shown in FIG. 5. The values of $\sigma\perp$ ranged from 62.3 to 243 mS/m (388% variation) with an average of 118 mS/m (SD=41.6 mS/m). The values of $\sigma_\parallel$ ranged from 54.3 to 185 mS/m (341% variation) with an average of 113 mS/m (SD=29 mS/m). The electrical conductivity values in the parallel and perpendicular directions showed anisotropy ($\chi^2$ test, p<0.01); the range of the measured anisotropy (i.e. $\sigma_\parallel/\sigma\perp$) was 0.63 to 1.51 (237% variation). Averaged together, conductivities perpendicular to the pial surface did not differ significantly from values parallel to the pial surface (P=0.622).

Example 3

DT-MRI Measurements

The values of proton diffusion in directions perpendicular (D$\perp$) and parallel (D$_\parallel$) to the cortical surface are shown in FIG. 5. The values of D$\perp$ ranged from 7.08 to 14.1 $\mu$cm$^2$/s (199% variation) with an average of 10.8 $\mu$cm$^2$/s (SD=1.69). The values of D$_\parallel$ ranged from 8.34 to 14.6 $\mu$cm$^2$/s (175% variation) an average of 11.8 $\mu$cm$^2$/s (SD=1.59). The magnitude of the average diffusion vector obtained from the parallel and perpendicular components ranged from 11.0 to 20.3 $\mu$cm$^2$/s with an average of 16.0 $\mu$cm$^2$/s (SD=0.224). The values of proton diffusion in parallel and perpendicular directions did not show significant anisotropy ($\chi^2$ test, p>0.05).

Example 4

Analysis and Comparison of MRI Diffusion and Brain Electrical Conductivity Measures Analysis found positive correlations between perpendicular (FIG. 7A) and parallel (FIG. 7B) diffusivities and the ratios of brain electrical conductivities ($\sigma_\parallel/\sigma\perp$) (FIG. 6). In addition, brain electrical conductivities perpendicular to the pial surface positively correlated with electrical conductivity parallel to the pia (FIG. 7C). DT-MRI diffusion perpendicular to the pial surface positively correlated with MRI diffusion parallel to the pia (FIG. 7D). The ratio of the electrical conductivities, positively correlated (R=0.484, p=0.016) with MRI diffusivity in the direction parallel to pia, and in the direction perpendicular to the pia (R=0.446, p=0.028). Brain electrical conductivities and ratios (FIG. 7E) and MRI diffusivity parallel to the pial surface did not show significant correlation. Brain electrical conductivity and MRI diffusivity perpendicular to the pial surface did not show correlations. The ratios of MRI diffusivities did not correlate significantly with MRI diffusivity in direction perpendicular to the pial surface (FIG. 7F). No correlation was observed between the ratios of electrical conductivities ($\sigma_\parallel/\sigma\perp$, i.e., measure of anisotropy in conductivity) and electrical conductivity parallel to the pial surface or the ratio of MRI diffusivities (D$_\parallel$/D$\perp$, i.e., measure of anisotropy in diffusivity) (FIG. 7E, FIG. 7G and FIG. 7H).

Example 5

Ionic Charge Transport Between Blockages

Sodium Cation Conduction in Freshly Excised Bulk Brain Tissue

Transient-dc and frequency-dependent electrical conductivities were analyzed between blocking electrodes. This analysis was extended to measurements of ions' transport in freshly excised bulk samples of human brain tissue whose complex cellular structure produces blockages. The associated ionic charge-carrier density and diffusivity were consistent with local values for sodium cations determined non-invasively in brain tissue by MRI (NMR) and diffusion-MRI (spin-echo NMR). The characteristic separation between blockages was estimated to be about 450 microns.

The electrical conductivity of freshly excised bulk samples of brain tissue was analyzed. Simple dc conductivity measurements exhibited a temporal decay. This temporal decay presumably resulted from the failure of ionic charge carriers to penetrate blockages. These dc conductivity measurements were complemented with conductivity measurements at low frequencies (6-1000 Hz). These measurements were analyzed to estimate the dc limit of the electrical conductivity of brain tissues' ionic charge carriers and the characteristic separation between blockages to their flow.

These estimates were consistent with sodium cation density and microscopic diffusivity determined non-invasively with MRI and diffusion-MRI.

Metallic electrodes generally functioned as extrinsic impenetrable barriers to ions' flow. In addition, intrinsic barriers resulted from structural features of an inhomogeneous material that preclude the passage of ions on the time scale of a transport measurement.

Figure 8:
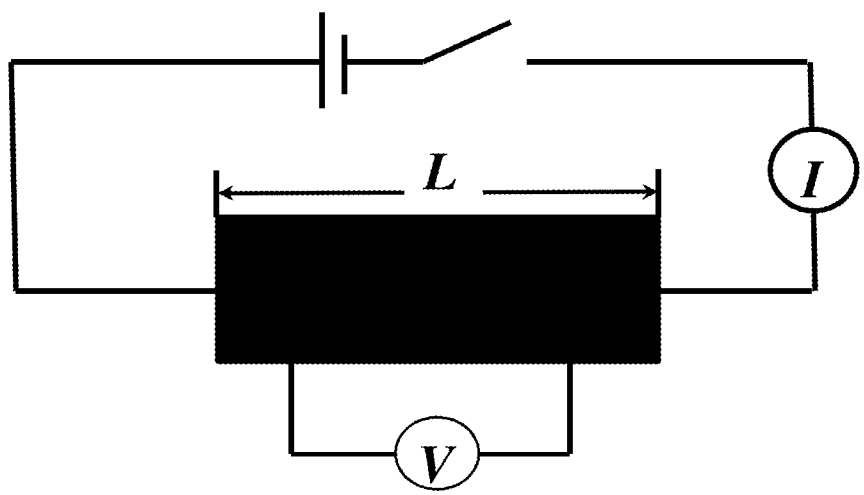
FIG. 8 depicts a schematic illustration of the circuit for measuring the dc conductivity of a sample between blocking electrodes separated by the distance L.

First the temporal decay of the dc conductivity obtained with a circuit like that depicted schematically in FIG. 8 was considered. Current will flow within a homogeneous sample having blocking electrodes immediately following application of a spatially constant electric field at a time defined as zero. Initially carriers' flow was characterized by their intrinsic dc conductivity $\sigma_{dc}$. The transient conductivity will decay from this initial value to zero as carriers were progressively stopped at the blocking electrode.

The non-uniform carrier density that results when the current flow ceases was determined by solving the corresponding charge-flow equation:

$$J(\infty) = 0 = \frac{nq^2D}{kT}E - qD\frac{dn}{dx},$$

where q, n and D respectively represent the carrier's charge, density and diffusion constant and E indicates the strength of the applied electric field. Here the carrier mobility $\mu$ is related to its diffusion constant by the Einstein relation, $\mu=qD/kT$, where k and T signify the Boltzmann constant and the temperature, respectively. Solving this first-order differential equation yields an expression for the resulting non-uniform spatial distribution of ions:

$$n(x,\infty)=n_e \exp(qEx/kT),$$

where the maximum ion density occurs at the interface at which ions are blocked from exiting the material x=L while the minimum ion density occurs at the opposing electrical contact at x=0. The relationship between the constant $n_e$ and the equilibrium carrier density $n_0$ was obtained by requiring constancy of the net number of ions:

$$n_0 L = n_e \int_0^L dx \exp(qEx/kT) = n_e \frac{\exp(qEL/kT)-1}{(qE/kT)}.$$

Thus, at arbitrarily long times the non-uniform distribution of ions approaches $$n(x,\infty) = n_0 \frac{(qEL/kT)}{\exp(qEL/kT)-1} \exp(qEx/kT).$$

Structures from which charge could neither enter nor escape served as "polarization centers." For example, an electronic charge carrier confined to an isolated pair of a semiconductor's dopants comprises a well-known polarization center (Pollak and Geballe, *Phys. Rev.* 1961, 122:1742). Application of a constant electric field shifted centers' confined charges. The conductivity associated with this polarization decreased after the electric field is applied as $\exp(-t/\tau)$, where $\tau$ denotes the center's characteristic relaxation time (Pollak and Geballe, *Phys. Rev.* 1961, 122:1742; Emin, *Phys. Rev. B.* 1992, 46:9419). This two-center relaxation time was calculated with the master equations in terms of the rates with which a carrier moves between sites.

A macroscopic sample whose mobile ions are confined by their inability to penetrate electrical contacts constitutes a macroscopic polarization center. In particular, with a sufficiently small carrier density carriers' mutual interactions can be ignored and the two-center polarization current to account for multiple ionic carriers with multiple polarization distances can be generalized. Then the macroscopic specimen's relaxation can be described with the classical diffusion equation in terms of carriers' diffusion constant (Reichl, *A Modern Course in Statistical Mechanics, University of Texas Press (Austin)*. 1980, Chapter 6. D).

Figure 9:
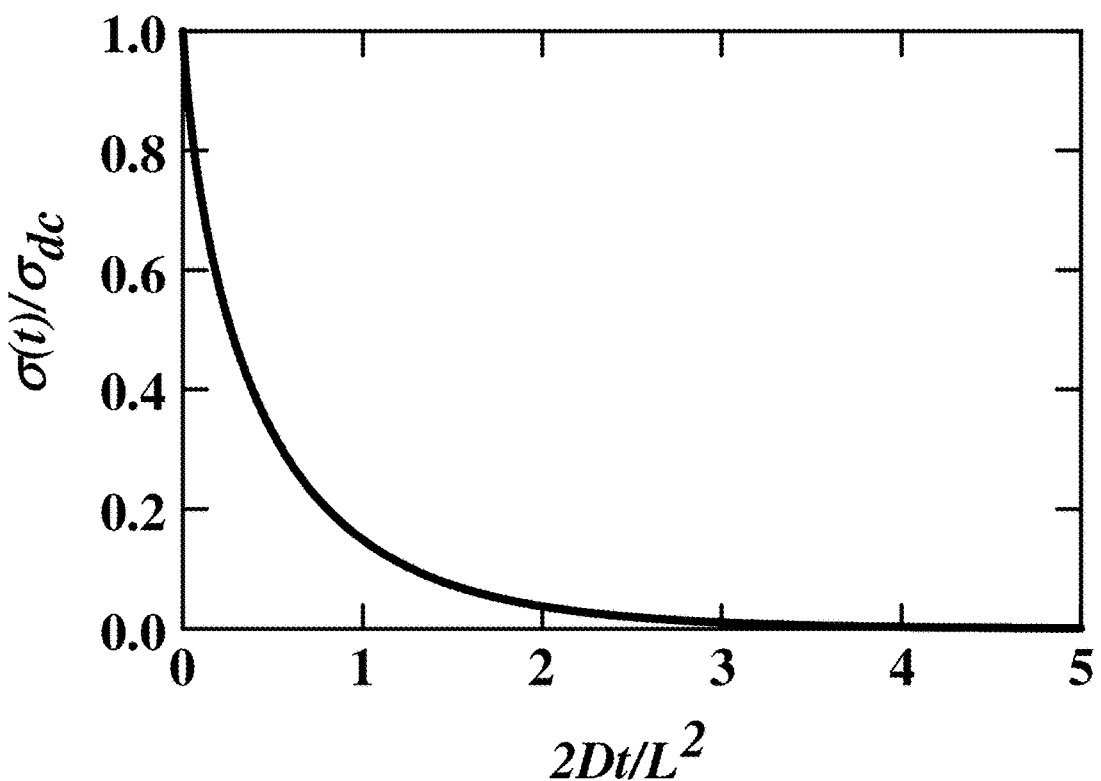
FIG. 9 depicts the conductivity at time t after initiating measurement of the dc conductivity plotted in units of the intrinsic dc conductivity $\sigma(0)=\sigma_{dc}$ versus t in units of $L^2/2D$, where D and L respectively denote the charge-carriers' diffusion constant and the separation between blocking electrodes.

The decaying conductivity was modelled as the sum of contributions that each arises from a carrier's diffusing to its blockage. With the time characterizing a carrier's diffusing a distance l to reach the blocking contact being $\tau(l)=l^2/2D$ this decaying conductivity becomes:

$$\sigma(t) = \frac{\sigma_{dc}}{L}\int_0^L dl\, e^{-t/\tau(l)}$$

$$= \frac{\sigma_{dc}}{L}\int_0^L dl\, e^{-2Dt/l^2}$$

$$= \sigma_{dc}\int_1^\infty du\, \frac{e^{-(2Dt/L^2)u}}{2u^{3/2}}$$

$$= \frac{\sigma_{dc}}{2} E_{3/2}(2Dt/L^2),$$

where $E_{3/2}(x)$ designates the established exponential integral defined in Eq. (5.1.4) of Abramowitz and Stegun (1964), *Handbook of Mathematical Functions, National Bureau of Standards Applied Mathematics Series* 55. As illustrated in FIG. 9, this transient conductivity monotonically falls from $\sigma_{dc}$ at t=0 toward zero with increasing time. In particular, this exponential integral's value at t=0 is given by $E_{3/2}(0)$ $=1/[(3/2)-1]=2$. In the complementary long-time limit, $2Dt/L^2 \gg 1$, the dc conductivity's temporal decay is described by:

$$\sigma(t) \cong \sigma_{dc}\left[\frac{\exp(-2Dt/L^2)}{(2Dt/L^2)+3/2}\right].$$

Distinctively, the relaxation time for interfacial conductivity produced by impenetrable electrodes decreases as the inter-electrode separation L is decreased. Temporal decay of the ionic conductivities of samples of gelatin gels doped with NaCl was observed. Relaxation times ($10^2$-$10^3$ sec) were found to fall as the sample length and the associated inter-electrode separation L is reduced. In these instances metallic electrodes functioned as extrinsic impenetrable barriers that dominated the temporal decay of the conductivity.

Figure 10:
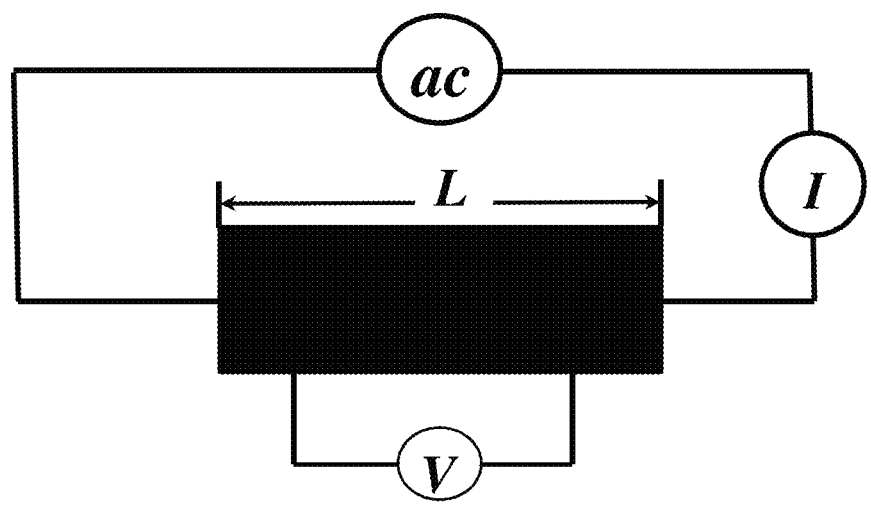
FIG. 10 depicts a schematic illustration of the circuit for measuring the ac conductivity of a sample between blocking electrodes separated by the distance L.

Measurement of the real part of the frequency-dependent conductivity, via a circuit like that schematically depicted in FIG. 10, provided an alternative way to study the transient decay of the conductivity. In particular, the real part of the frequency-dependent ac conductivity corresponding to this temporally decaying current was obtained from the Fourier transforms of the current density and the strength of the applied electric field, J(t) and E, respectively:

$$\text{Re}[\sigma(\omega)] \equiv \text{Re}\left[\frac{J(\omega)}{E(\omega)}\right]$$

-continued $$= \frac{\int_0^\infty dt e^{i\omega t} J(t)}{E \int_0^\infty dt e^{i\omega t}}$$

$$= \frac{\int_0^\infty dt e^{i\omega t} J(t)}{iE/\omega}$$

$$= \omega \int_0^\infty dt \sigma(t) \sin(\omega t).$$

Evaluating this formula for the model yields:

$$\text{Re}[\sigma(\omega)] = \frac{\sigma_{dc}}{L} \omega \int_0^L dl \int_0^\infty dt e^{-2Dt/l^2} \sin(\omega t)$$

$$= \frac{\sigma_{dc}}{L} \int_0^L dl \left[ \frac{\left(\frac{\omega l^2}{2D}\right)^2}{1 + \left(\frac{\omega l^2}{2D}\right)^2} \right]$$

$$= \sigma_{dc} \sqrt{\frac{2D}{\omega L^2}} \int_0^{\sqrt{\frac{\omega L^2}{2D}}} dy \left[ \frac{y^4}{1 + y^4} \right].$$

Figure 11:
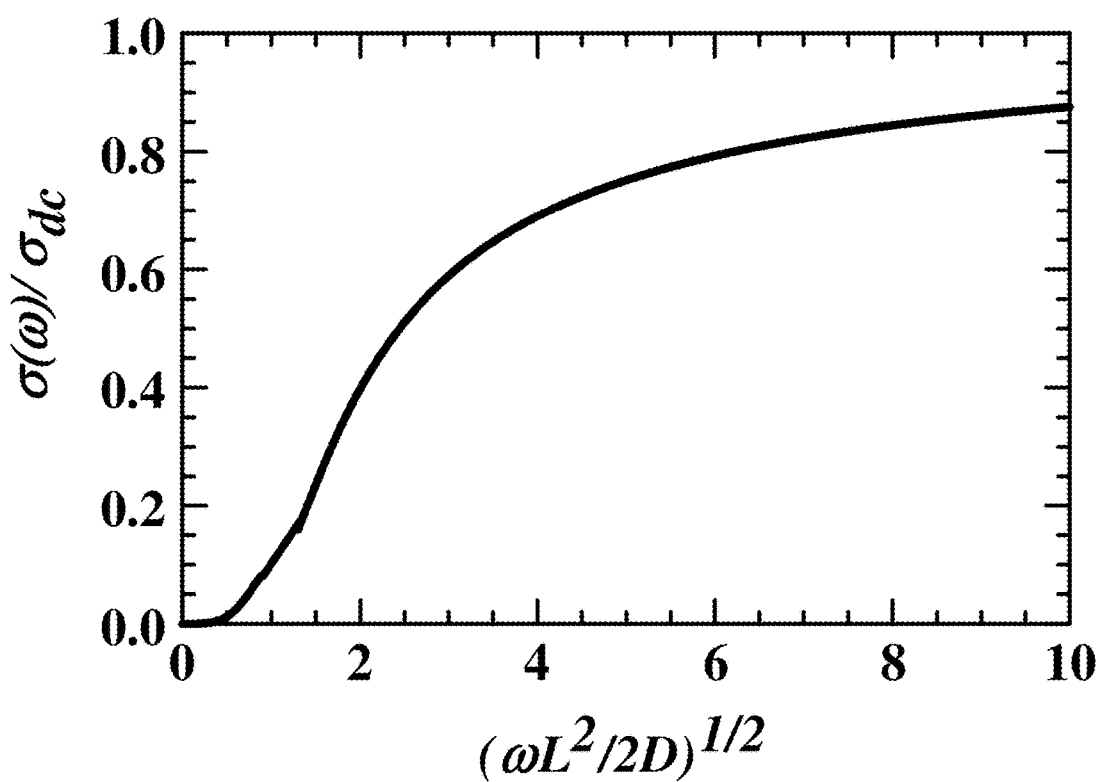
FIG. 11 depicts the ac conductivity, $\sigma(\omega)$ at applied frequency $\omega$, in units of the initial dc conductivity $\sigma_{dc}$ plotted versus the square-root of $\omega$ in units of $2D/L^2$, where D and L respectively denote the charge-carriers' diffusion constant and the separation between blocking electrodes.
Figure 12A:
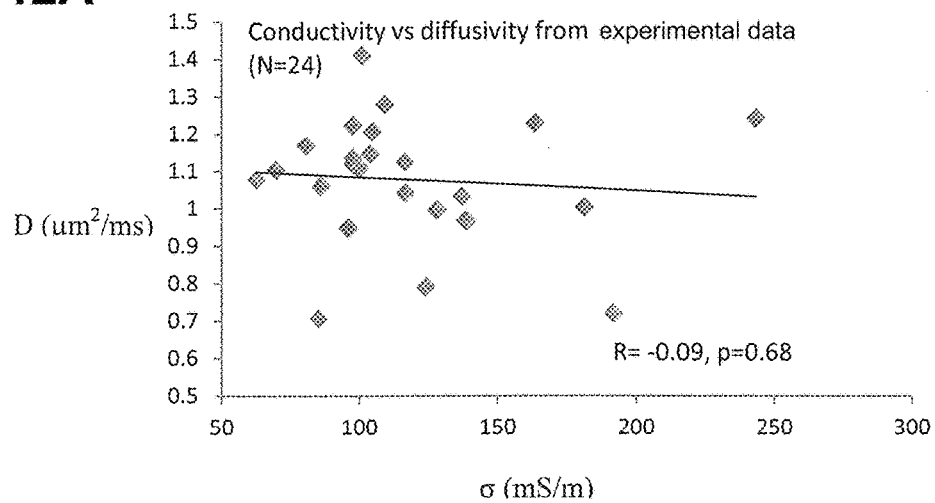
FIG. 12A-12B are plots of electrical conductivity versus water proton diffusivity (D; in $\mu m^2/ms$) (FIG. 12A), and ion concentration versus water proton diffusivity (FIG. 12B). The graph (FIG. 12A) of electrical conductivity as measured in 24 surgical patients in relation to tissue water proton diffusivity, as assumed to be linear by all existing methods of DTI brain conductivity measurements, shows no significant correlation (R=−0.09, p=0.68) a). Once this method is applied to the described model using the water proton diffusivities the resulting tissue ion concentration (n; in mM) shows nearly perfect fit (R=0.87, p<001) (FIG. 12B). The predicted brain tissue ion concentration is consistent with the range and variation of tissue sodium concentration in normal and diseased brain tissues.
Figure 12B:
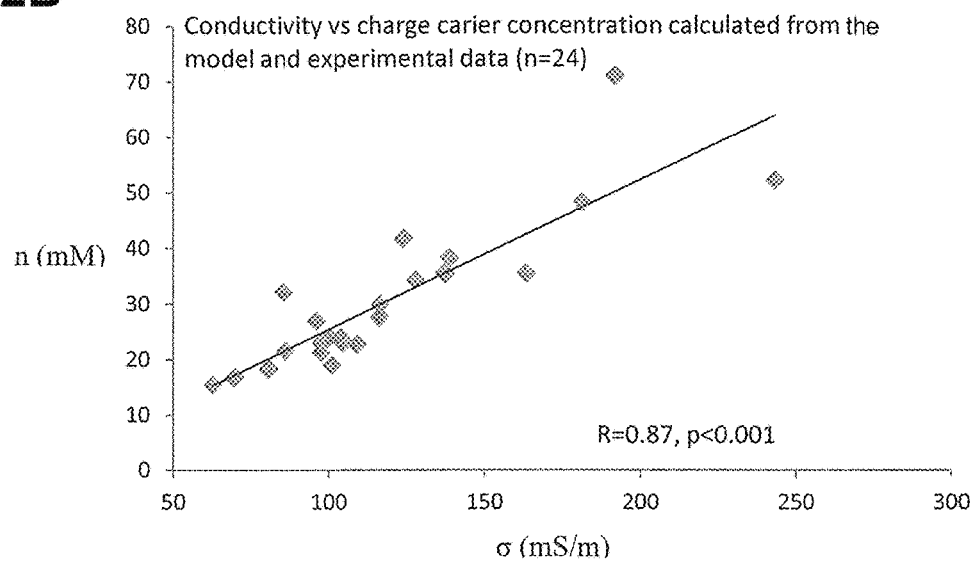

FIG. 11 displays a plot of $\text{Re}[\sigma(\omega)]$ versus $(\omega L^2/2D)^{1/2}$. As expected, $\text{Re}[\sigma(\omega)]$ vanished in the dc limit, $\omega \rightarrow 0$, since carriers cannot penetrate the electrodes. $\text{Re}[\sigma(\omega)]$ remained finite at finite applied frequencies. In particular, $\text{Re}[\sigma(\omega)]$ manifested its strongest frequency dependence when $\omega \sim 2D/L^2$. At higher frequencies, $\omega \gg 2D/L^2$, the frequency dependence of the measured conductivity weakened. In this domain the measured conductivity asymptotically approached the material's intrinsic dc conductivity $\sigma_{dc}$:

$$\text{Re}[\sigma(\omega)] \cong \sigma_{dc} \left[ 1 - \left(\frac{56}{45}\right) \sqrt{\frac{2D}{\omega L^2}} \right].$$

Samples (~1 cm³) of tissue freshly excised from various brain locations during surgeries on pediatric epilepsy patients (Akhtari et al., *Brain Topogr.* 2006, 18:281; Akhtari et al., *Brain Topogr.* 2010, 23: 292) were extensively studied. Some of the salient features of just the bulk conductivity measurements of Akhtari et al., *Brain Topogr.* 2006, 18:281 and Akhtari et al., *Brain Topogr.* 2010, 23: 292 are summarized. Application of a dc electric field generated a transient conductivity that decays significantly within minutes, $\tau \sim 10^2$ sec. In addition, the ac conductivity measured between 6-1000 Hz increased very slowly with increasing frequency. These results indicated that $\tau \sim L^2/2D \gg 1/\omega$. Thus the frequencies of the ac conductivity measurements were too high to observe the relatively slow transient decay. Rather, these ac conductivity measurements provided an estimate of the initial dc conductivity: $\sigma dc > \sigma(1000 \text{ Hz})$. The measured dc conductivity at room temperature was $\sigma dc \sim 0.15$ S/m.

The average Na⁺ concentration measured in human brain tissue is about $2.4 \times 10^{25}$ m⁻³ (about 40 mM) (Madelin et al., *Scientific Reports.* 2014, 4:4763). A similar average Na+ concentration was found in the brain tissue of healthy rats. In particular, the extracellular and intracellular concentrations of sodium reported for healthy rat brain tissue were 140 mM and 10 mM, respectively, with the extracellular volume fraction being ~0.2 (Goodman et al., *Magnetic Resonance in Medicine.* 2005, 53:1040).

Taken together, the density of Na cations $n_{Na}$ and $\sigma_{dc}$ provided an estimate of their diffusion constant $D_o = [(kT/q)/n_{Na}q]\sigma_{dc}$. In particular, associating the measured dc conductivity with the typical density of human brains' Na cations yielded their diffusion constant at room temperature, $kT = 2.5 \times 10^{-2}$ V, $D_o = [(2.5 \times 10^{-2} \text{ V})/(2.4 \times 10^{-5} \text{ m}^{-3})(1.6 \times 10^{-19} \text{ C})](1.5 \times 10^{-1} \text{ S/m}) \cong 10^{-9}$ m²/sec. In addition, the room-temperature diffusion constants measured with proton-diffusion MRI for the protons of human brain tissue's water molecules were also ~$10^{-9}$ m²/sec (Akhtari et al., *Brain Topogr.* 2010, 23: 292). The diffusion of Na cations in water was associated with substantial reorientation of some of the surrounding water molecules (Hirbar et al., *J. Am. Chem. Soc.* 2002, 124:12302). Furthermore, diffusion-MRI measurements on Na nuclei in living rat brain also yielded anisotropic local apparent diffusion constants of ~1 (μm)²/ms = $10^{-9}$ m²/sec (Goodman et al., *Magnetic Resonance in Medicine.* 2005, 53:1040). Similarly, the local anisotropic diffusion constants inferred from proton diffusion-MRI measurements in rat brain were ~$10^{-9}$ m²/sec (Sekino et al., *Bioelectromagnetics.* 2009, 30:489). Thus, the diffusion constant of sodium in freshly excised bulk human brain tissue estimated from measurements of its electrical conductivity was comparable to local values determined non-invasively with MRI and diffusion-MRI.

The slow transient decay of human brain tissues' dc conductivity was attributed to sodium cations moving between blockages and provided an estimate of the characteristic separation between them, $L_{94} = (2D_o \tau)^{1/2}$. With $D_o = 10^{-9}$ m²/sec and $\tau = 10^2$ sec it was found that $L_o = (20 \times 10^{-8} \text{ m}^2)^{1/2} \approx 4.5 \times 10^{-4}$ m = 450 μm. The smallness of $L_o$ relative to the sample size $L \sim 10^{-2}$ m indicated that Na cations' transport was primarily limited by blockages within the material rather than by the experiment's electrodes. For example, ions diffusing through intercellular fluid must navigate through a dense distribution of cells with diameters up to 40 μm (Sekino et al., *Bioelectromagnetics.* 2009, 30:489; Holsheimer, *Exp. Brain Res.* 1987, 67:402). All told, sodium cations would appear to diffuse among many cells in the brain's complex inhomogeneous medium before being effectively blocked.

In summary, the temporal decay of ionic charge carriers' dc conductivity and ac conductivity that resulted from simple blockages was analyzed. The analysis was applied to electrical conductivity measurements on gelatin gels doped with NaCl and on freshly excised bulk brain tissue. The temporal decay of the conductivities of the NaCl-doped gelatin gels appeared extrinsic, dominated by ions encountering impenetrable electrodes. The charge-carrier concentration and diffusion constant of the freshly excised brain tissue were consistent with those of Na cations determined with non-invasive MRI measurements. The temporal decay of the conductivity measurements of freshly excised bulk brain tissue appeared intrinsic, dominated by effective blockages associated with tortuous ionic transport through complex inhomogeneous brain tissue.

Example 6

Figure 13A:
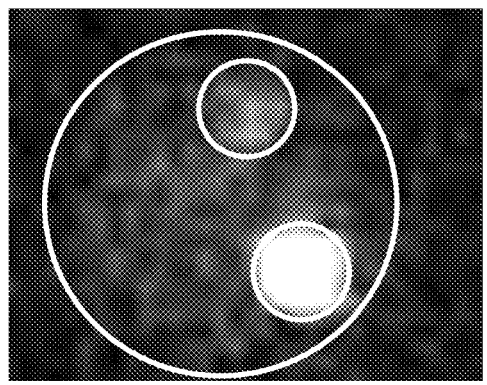
FIG. 13A-13B are images of sodium MRI scans of brain tissue samples, according to embodiments of the present disclosure.
Figure 13B:
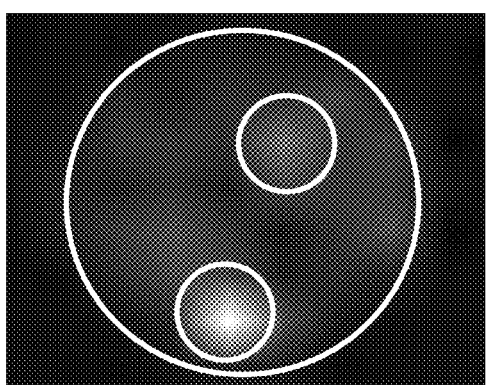

Conductivities (σ) of 4 brain samples were measured immediately after intracranial excision of the brain samples while maintaining a temperature of 20° C. The preoperative apparent diffusion coefficient (ADC) values of the excised tissues were measured on preoperative diffusion tensor imaging (DTI) scans of the same patients. The sodium concentration values of the excised tissues were measured using inductively coupled plasma mass spectrometry (ICP- MS) in all tissues and using sodium MRI scans in 2 brain samples according to embodiments of the present disclosure. The sodium MRI scans were acquired while 2 plastic tubes containing saline solutions of 0.9% and 1.8% concentrations were inserted in the brain tissue samples. FIGS. 13A-13B show the sodium concentration scans as visualized by MRI.

FIG. 13A shows a sodium MRI of Sample 1. Brain tissue is indicated by the large outer white circle. The top inner white circle indicates the saline sample with a concentration of 0.9%, and the bottom inner white circle indicates the saline sample with a concentration of 1.8%.

FIG. 13A shows a sodium MRI of Sample 2. Brain tissue is indicated by the large outer white circle. The top inner white circle indicates the saline sample with a concentration of 0.9%, and the bottom inner white circle indicates the saline sample with a concentration of 1.8%.

The sodium concentration of the tissue samples was calculated by comparing the tissue signal intensity with that of the known sodium concentration of the saline tubes. Table 1 shows the sodium concentrations obtained from the MRI scans and those obtained from ICP-MS, as well as measured apparent diffusion coefficient (ADC) values in both saline samples from Sample 1 and Sample 2, and also the measured and calculated conductivity values.

TABLE 1

| | Milli molar (mM) [Na] MRI | mM [Na] ICPMS | ADC m$^2$/s × 10$^{-9}$ | $\sigma_{measured}$ (S/m) | $\sigma_{model}$ |
|---|---|---|---|---|---|
| Sample 1 (0.9% saline) | 65 | 67 | 0.36 | 0.103 (0.0063) | 0.094 |
| Sample 1 (1.8% saline) | 90 | 90 | 0.36 | 0.119 (0.0063) | 0.126 |
| Sample 2 (0.9% saline) | — | 65 | 0.65 | 0.235 (0.007) | 0.240 |
| Sample 2 (1.8% saline) | — | 67 | 0.65 | 0.210 (0.0069) | 0.247 |

These data show excellent agreement between the measured electrical conductivity of the brain tissues and those determined by the methods and systems of the present disclosure.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A non-invasive method of generating a conductivity map of an in vivo tissue, the method comprising:
    a) measuring a concentration of a carrier ion in the tissue using magnetic resonance imaging (MRI);
    b) measuring a water proton diffusivity (D) in the tissue using diffusion tensor MRI (DT-MRI); and
    c) generating a conductivity map of the tissue, using the formula:

$$\sigma = (D\, n\, q^2)/kT$$

wherein σ is conductivity, D is the water proton diffusivity, n is the concentration of the carrier ion, q is a charge of the carrier ion, k is Boltzmann constant, and T is temperature in degrees Kelvin.

2. The method of claim 1, wherein the tissue is brain tissue.

3. The method of claim 1, wherein the tissue is heart tissue.

4. The method of claim 1, wherein the concentration of the carrier ion and the water proton diffusivity are measured using a single coil.

5. The method of claim 1, wherein the carrier ion is selected from a sodium ion, a chloride ion, a potassium ion, and a calcium ion.

6. The method of claim 1, wherein the DT-MRI is performed at 0.3 T.

7. The method of claim 1, wherein the DT-MRI is performed at 1.5 T.

8. The method of claim 1, wherein the DT-MRI is performed at 3 T.

9. The method of claim 1, wherein the DT-MRI is performed at 7 T.

10. The method of claim 1, wherein the DT-MRI is performed at 9 T.

11. The method of claim 1, wherein the DT-MRI is performed at 12 T.

12. A system for generating a conductivity map of an in vivo tissue, the system comprising:
    a) a magnetic resonance imaging (MRI) device configured to measure a concentration of a carrier ion in the tissue and a water proton diffusivity (D) in the tissue;
    b) a processor; and
    c) a non-transient memory comprising instructions that, when executed by the processor, cause the processor to generate a conductivity map of the tissue based on measurements from the MRI device, wherein the instructions comprise the formula:

$$\sigma = (D\, n\, q^2)/kT$$

wherein σ is conductivity, D is the water proton diffusivity, n is the concentration of the carrier ion, q is the charge of the carrier ion, k is Boltzmann constant, and T is temperature in degrees Kelvin.

13. The system of claim 12, further comprising a data storage that is configured to store conductivity map data.

14. The system of claim 12, further comprising a user interface and a data connector that transmits data between the processor and the user interface.

15. The system of claim 12, wherein the MRI device comprises a coil for measuring the concentration of the carrier ion in the tissue.

16. The system of claim 12, wherein the MRI device comprises electronic devices configured to generate frequencies, gradients and pulses for measuring the concentration of the carrier ion in the tissue.

17. The system of claim 12, wherein the MRI device comprises a coil for measuring the water proton diffusivity (D) in the tissue.

18. The system of claim 12, wherein the MRI device comprises a single coil for measuring the concentration of the carrier ion in the tissue and the water proton diffusivity (D) in the tissue.

* * * * *